US009255843B2

(12) United States Patent
Yu et al.

(10) Patent No.: US 9,255,843 B2
(45) Date of Patent: Feb. 9, 2016

(54) POROUS SERS ANALYTICAL DEVICES AND METHODS OF DETECTING A TARGET ANALYTE

(71) Applicants: Wei Wen Yu, College Park, MD (US); Ian M. White, Ellicott City, MD (US)

(72) Inventors: Wei Wen Yu, College Park, MD (US); Ian M. White, Ellicott City, MD (US)

(73) Assignee: University of Maryland, College Park, College Park, MD (US)

( * ) Notice: Subject to any disclaimer, the term of this patent is extended or adjusted under 35 U.S.C. 154(b) by 455 days.

(21) Appl. No.: 13/626,421

(22) Filed: Sep. 25, 2012

(65) Prior Publication Data
US 2013/0107254 A1    May 2, 2013

Related U.S. Application Data

(60) Provisional application No. 61/539,334, filed on Sep. 26, 2011, provisional application No. 61/585,990, filed on Jan. 12, 2012, provisional application No. 61/603,800, filed on Feb. 27, 2012.

(51) Int. Cl.
| | | |
|---|---|---|
| *G01J 3/44* | (2006.01) | |
| *G01N 21/552* | (2014.01) | |
| *G01N 21/65* | (2006.01) | |
| *B82Y 30/00* | (2011.01) | |

(52) U.S. Cl.
CPC ............... *G01J 3/44* (2013.01); *G01N 21/554* (2013.01); *G01N 21/658* (2013.01); *B82Y 30/00* (2013.01)

(58) Field of Classification Search
CPC ..... G01N 21/658; G01N 21/554; B82Y 30/00
See application file for complete search history.

(56) References Cited

U.S. PATENT DOCUMENTS

| | | | |
|---|---|---|---|
| 4,674,878 A | | 6/1987 | Vo-Dinh |
| 5,255,067 A | * | 10/1993 | Carrabba et al. ............... 356/301 |
| 6,623,977 B1 | | 9/2003 | Farquharson et al. |
| 6,970,239 B2 | * | 11/2005 | Chan et al. ..................... 356/301 |
| 7,361,313 B2 | * | 4/2008 | Chan et al. ..................... 438/57 |
| RE40,299 E | * | 5/2008 | Bruinsma et al. .............. 423/335 |
| 7,393,691 B2 | | 7/2008 | Farquharson et al. |
| 7,460,224 B2 | * | 12/2008 | Wang et al. .................... 356/301 |
| 7,787,117 B1 | | 8/2010 | Leona et al. |
| 7,888,129 B2 | | 2/2011 | Hulteen et al. |
| 7,963,646 B2 | | 6/2011 | Magdassi et al. |
| 8,243,271 B2 | | 8/2012 | Jablonski et al. |
| 2003/0059820 A1 | | 3/2003 | Vo-Dinh |
| 2004/0161369 A1 | * | 8/2004 | Chan et al. .................. 422/82.05 |
| 2004/0179195 A1 | * | 9/2004 | Su et al. ......................... 356/301 |

(Continued)

OTHER PUBLICATIONS

Chang H Lee, "Directed assembly of gold nanorods using aligned electrospun polymer nanofibers for highly efficient SERS substrates", May 26, 2011.*

(Continued)

*Primary Examiner* — Kara E Geisel
*Assistant Examiner* — Maurice Smith
(74) *Attorney, Agent, or Firm* — William C. Schrot; AuerbachSchrot LLC

(57) ABSTRACT

A surface enhanced Raman spectroscopy (SERS) analytical device includes a substrate having a porous structure, and a plurality of plasmonic nanoparticles embedding in the porous structure and forming a sensing region. A method of detecting a target analyte in a sample includes contacting the sample with the substrate, whereby the target analyte, if present in the sample, is concentrated in the sensing matrix. The substrate may then be analyzed using SERS detection equipment.

26 Claims, 14 Drawing Sheets

(56) References Cited

U.S. PATENT DOCUMENTS

| | | | |
|---|---|---|---|
| 2004/0191921 A1 | 9/2004 | Farquharson et al. | |
| 2005/0221333 A1* | 10/2005 | Sundararajan et al. | 435/6 |
| 2006/0021468 A1* | 2/2006 | Ah et al. | 75/371 |
| 2006/0038979 A1 | 2/2006 | Natan et al. | |
| 2006/0275541 A1* | 12/2006 | Weimer | 427/96.1 |
| 2008/0044856 A1* | 2/2008 | Amiss et al. | 435/69.1 |
| 2008/0171656 A1* | 7/2008 | Wang et al. | 502/326 |
| 2009/0257056 A1* | 10/2009 | Demirel et al. | 356/301 |
| 2011/0026019 A1 | 2/2011 | Tyagi et al. | |
| 2012/0236298 A1* | 9/2012 | Stuke et al. | 356/301 |

OTHER PUBLICATIONS

Amy M. Michaels, "Surface Enhanced Raman Spectroscopy of Individual Rhodamine 6G Molecules on Large Ag Nanocrystals" Jun. 22, 1999.*

Dian He, "Large-Scale Synthesis of Flexible Free-Standing SERS Substrates with High Sensitivity: Electrospun PVA NanofibersEmbedded with Controlled Alignment of Silver Nanoparticles", ACSNANO, Nov. 23, 2009.*

Scriven, L.E. (1988) "*Physics and Applications of Dip Coating and Spin Coating,*" Mat. Res. Soc. Symp. Proc. vol. 121, pp. 717-729.

Chan, S. et al. (2003) "*Surface-Enhanced Raman Scattering of Small Molecules from Silver-Coated Silicon,*" Adv. Mater. 15(19):1595-1598.

Hoppmann, E.P. et al. (2013) "Highly Sensitive and flexible inkjet printed SERS sensors on paper," Methods 63:219-224.

Abe K. et al. (2008) "*Inkjet-Printed Microfluidic Multianalyte Chemical Sensing Paper,*" Anal. Chem. 80:6928-6934.

Bello et al. (1989) "*Silver-Coated Alumina as a New Medium for Surface-Enhanced Raman Scattering Analysis,*" Applied Spectroscopy 43(8):1325-1330.

Berthod et al. (1988) "*Analysis by surface enhanced Raman spectroscopy on silver hydrosols and silver coated filter papers,*" J. Pharma. & Biomed. Anal. 6:599-608.

Cabalin L.M. et al. (1995) "*Fast spatially revolved surface-enhanced Raman spectrometry on a silver coated filter paper using charge-coupled device detection,*" Analytica Chimica Acta 310:337-345.

Cabalin L.M. (1995) "*Sample illumination configurations for spatially resolved Raman spectrometry using a charge-coupled device detector,*" Talanta 42:1379-1383.

Cho H. et al. (2009) "*Label-free and highly sensitive biomolecular detection using SERS and electrokinetic preconcentration,*" Lab Chip 9:3360-3363.

Choi D. et al. (2009) "*Additional amplifications of SERS via an optofluidic CD-based platform,*" Lab Chip 9:239-243.

Choi I. et al. (2011) "*Size-selective concentration and label-free characterization of protein aggregates using a Raman active nanofluidic device,*" Lab Chip. 11:632-638.

Dungchai W. et al. (2009) "*Electrochemical Detection for Paper-Based Microfluidics,*" Anal. Chem 81:5821-5826.

Erol et al (2009) "*SERS Not to Be Taken for Granted in the Presence of Oxygen,*" J. Am. Chem. Soc. 131:7480-7481.

FDA (2008) FDA Issues Interim Safety and Risk Assessment of Melamine and Melamine-related Compounds in Food.

Figueroa et al. (2012) "Fabrication of Flexible and Porous Surface Enhanced Raman Scattering (SERS) Substrates using Nanoparticle Inks," AIP Conf. Proc. 1461:47-53.

Gamby J. et al. (2009) "*Polycarbonate microchannel network with carpet of Gold NanoWires as SERS-active device,*" Lab Chip 9:1806-1808.

Han B. et al. (2011) "Application of silver-coated magnetic microspheres to a SERS-based optofluidic sensor," J. of Phys. Chem. C 115:6290-6296.

Hossain S.M.Z. et al. (2009) "*Development of a Bioactive Paper Sensor for Detection of Neurotoxins Using Piezoelectric Inkjet Printing of Sol-Gel-Derived Bioinks,*" Anal. Chem. 81:5474-5483.

Huh Y.S., Chung A.J., Erickson D. (2009) "*Surface Enhanced Raman spectroscopy and its application to molecular and cellular analysis,*" Microfluid Nanofluid 6:285-297.

Huh Y.S. et al. (2009) "*Enhanced on-chip SERS based biomolecular detection using electrokinetically active microwells,*" Lab Chip 9:433-439.

Khan M.S. et al. (2010) "*Biosurface engineering through ink jet printing,*" Colloids Surf., B. 75:441-447.

Kneipp K. et al. (1997) "*Single Molecule Detection Using Surface-Enhanced Raman Scattering (SERS),*" Phys. Rev. Lett. 78:1667-1670.

Laserna J.J. et al. (1988) "*Surface-Enhanced Raman Spectrometry on a Silver-Coated Filter Paper Substrate,*" Analytica Chimica Acta 208:21-30.

Laserna J.J. et al. (1989) "*Mixture Analysis and Quantitative Determination of Nitrogen-Containing Organic Molecules by Surface-Enhanced Raman Spectrometry,*" Anal. Chem. 61:1697-1701.

Lee P.C. and Meisel D. (1982) "*Adsorption and Surface-Enhanced Raman of Dyes on Silver and Gold Sols,*" J. Phys. Chem. 86:3391-3395.

Lee, A.S. et al. (1994) "*Surface-Enhanced Raman Spectra Using Silver-Coated Paper Substrates,*" J. Raman Spectroscopy 25:209-214.

Li YS et al. (1992) "*Surface-Enhanced Raman Spectroscopy Using a Silver Coated Capillary Substrate,*" Proc. SPIE, Applied Spectroscopy in Materials Science II 1636:129-137.

Li X. et al. (2010) "*Fabrication of paper-based microfluidic sensors by printing,*" Colloids Surf. B. 76:564-570.

Lim C. et al. (2010) "*Optofluidic platforms based on surface-enhanced Raman scattering,*" J. Analyst 135:837-844.

Lin X-M et al. (2009) "*Surface-enhanced Raman spectroscopy: substrate-related issues,*" Anal. Bioanal. Chem. 394:1729-1745.

Liu G.L. and Lee L.P. (2005) "*Nanowell surface enhanced Raman scattering arrays fabricated by solf-lithography for label-free biomolecular detections in integrated microfluidics,*" Appl. Phys. Lett. 87:074101.

Martinez A.W. et al. (2008) "*Simple Telemedicine for Developing Regions: Camera Phones and Paper-Based Microfluidic Devices for Real-Time, Off-Site Diagnosis,*" Anal. Chem. 80:3699-3707.

Martinez A.W. et al. (2008) "*Three-dimensional microfluidic devices fabricated in layered paper and tape,*" Proc. Natl. Acad. Sci. 105:19606-19611.

Martinez, A.W. et al. (2010) "*Diagnostics for the developing world: microfluidic paper-based analytical devices,*" Analytical Chemistry, 82:3-10.

Martinez A.W. et al. (2008) "*FLASH: A rapid method for prototyping paper-based microfluidic devices,*" Lab Chip 8:2146-2150.

Measor P. et al. (2007) "On-chip surface-enhanced Raman scattering detection using integrated liquid-core waveguides," Appl. Phys. Lett. 90:211107.

Nie S. and Emory S.R. (1997) "*Probing Single Molecules and Single Nanoparticles by Surface-Enhanced Raman Scattering,*" Science 275:1102-1106.

Nie Z. et al. (2010) "*Electrochemical sensing in paper-based microfluidic devices,*" Lab Chip 10:477-483.

Niu et al. (2006) "*Surface-enhanced Raman scattering of single-walled carbon nanotubes on silver-coated and gold-coated filter paper,*" J. Colloid and Interface Sci. 303:224-228.

Park S-M et al. (2009) "*A method for nanofluidic device prototyping using elastomeric collapse,*" Proc. Natl. Acad. Sci. 106:15549-15554.

Pelton R. (2009) "*Bioactive paper provides a low-cost platform for diagnostics,*" Trends Anal. Chem. 28:925-942.

Qi H. et al. (2010) "*The effect of size and size distribution on the oxidation kinetics and plasmonics of nanoscale Ag particles,*" Nanotechnology 21:215706.

Quang L.X. et al. (2008) "*A portable surface-enhanced Raman scattering sensor integrated with a lab-on-a-chip for field analysis,*" Lab Chip 8:2214-2219.

Strehle K.R. et al. (2007) "*A Reproducible Surface-Enhanced Raman Spectroscopy Approach. Online SERS Measurements in a Segmented Microfluidic System,*" J. Anal. Chem. 79:1542-1547.

Tran, C.D. (1984) "*Subnanogram Detection of Dyes on Filter Paper by Surface-Enhanced Raman Scattering Spectrometry,*" Anal. Chem. 56:824-826.

Tran, C.D. (1984) "*In situ identification of paper chromatogram spots by surface enhanced Raman scattering,*" J. Chromatography 292:432-438.

(56) References Cited

OTHER PUBLICATIONS

Vo-Dinh et al. (1984) "*Surface-Enhanced Raman Spectrometry for Trace Organic Analysis*," Anal. Chem. 56:1667-1670.

Walsh, R.J. et al. (2001) "*Silver Coated Porous Alumina as a New Substrate for Surface-Enhanced Raman Scattering*," Applied Spectroscopy 55:1695-1700.

Wang G. et al. (2009) "*Surface-enhanced Raman scattering in nanoliter droplets: towards high-sensitivity detection of mercury (II) ions*," J. Anal. Bioanal. Chem. 394:1827-1832.

Wang M. et al. (2009) "*Optofluidic device for ultra-sensitive detection of proteins using surface-enhanced Raman spectroscopy*," Microfluid Nanofluid 6:411-417.

White I.M. et al. (2007) "*SERS-based detection in an optofluidic ring resonator platform*," Optics Express 15(25):17433-17442.

Wu, E et al. (2003) "*The adsorption behavior of p-hydroxybenzoic acid on a silver-coated filter paper by surface enhanced Raman scattering*," J. Colloid and Interface Sci. 265:234-238.

Yang X. et al. (2010) "*High-sensitivity molecular sensing using hollow-core photonic crystal fiber and surface-enhanced Raman scattering*," J. Opt. Soc. Am. A. 27:977-984.

Yin Y. et al. (2011) "*Recent developments in optofluidic-surface-enhance Raman scattering systems: Design, assembly, and advantages*," J. Mater. Res. 26:170-185.

Yu W.W. et al. (2010) "*Inkjet Printed Surface Enhanced Raman Spectroscopy Array on Cellulose Paper*," Anal. Chem. 82:9626-30.

Yu W.W. et al. (2012) "*A simple filter-based approach to surface enhanced Raman spectroscopy for trace chemical detection*," Analyst 137(5):1168-1173.

Yu W.W. et al. (2012) "*Inkjet-Fabricated SERS-Active Swab-Dipstick*," Imaging and Appl Optics Technical Digest.

Zavalin, A. et al. (2005) "*Surface-Enhanced Raman Spectroscopy Using Silver-Coated Porous Glass-Ceramic Substrates*," Applied Spectroscopy 59:782-786.

Zhao W.A. et al. (2008) "*Paper-Based Bioassays Using Gold Nanoparticle Colorimetric Probes*," Anal. Chem. 80:8431-8437.

\* cited by examiner

POROUS SERS ANALYTICAL DEVICES AND METHODS OF DETECTING A TARGET ANALYTE

STATEMENT REGARDING FEDERALLY SPONSORED RESEARCH OR DEVELOPMENT

This work was supported by the National Institutes of Health as provided for by the terms of K25EB006011. The US government has certain rights in this invention.

CROSS-REFERENCE TO RELATED APPLICATIONS

This application is based on U.S. Provisional Patent Application Ser. No. 61/539,334, filed Sep. 26, 2011, application Ser. No. 61/585,990, filed Jan. 12, 2012, and application Ser. No. 61/603,800, filed Feb. 27, 2012, which applications are all incorporated herein by reference in their entireties and to which priority is claimed.

FIELD OF THE INVENTION

The present invention relates to a low-cost surface enhanced Raman spectroscopy (SERS) analytical device, methods of forming a SERS analytical device, and methods of detecting a target analyte.

BACKGROUND OF THE INVENTION

Detection of trace chemicals in solid and liquid samples may be achieved by methods that combine chromatography techniques with mass spectrometry. While sensitive, such methods are labor intensive, time consuming, and costly. They also require expensive and bulky equipment, and hence are not portable.

Surface enhanced Raman Spectroscopy (SERS) offers an attractive alternative for chemical analysis. SERS is a powerful technique for chemical and biomolecular identification. Typically, a SERS analysis involves spotting a μL-volume of sample onto a nanofabricated SERS substrate, allowing it to dry, and then detecting the Raman scattering. Due to the optical and chemical enhancement of nanostructures, single molecule identification has been demonstrated with SERS.

Unfortunately, the high cost and complications associated with the fabrication of conventional SERS-active substrates have prevented the wide use of SERS. Furthermore, these substrates exhibit limited shelf life, with progressive reduction in SERS activity due to oxidation of the nanostructures (see Erol M. et al. (2009), "*SERS Not To Be Taken for Granted in the Presence of Oxygen,*" J. Am. Chem. Soc. 131:7480-1).

To make SERS more applicable, attempts have been made to combine microfluidic techniques with SERS (see Huh Y. S. et al. (2009), supra, Microfluid. Nanofluid. 6:285-297; Lim C. et al. (2010) "*Optofluidic platforms based on surface-enhanced Raman scattering,*" J. Analyst 135:837-844; Yin Y. et al. (2011) J. Mater. Res. 26:170-185; Huh Y. S. et al. (2009) "*Enhanced on-chip SERS based biomolecular detection using electrokinetically active microwells,*" Lab Chip 9:433-439; Measor P. et al. (2007) Appl. Phys. Lett. 90:211107; Yang X. et al. (2010) J. Opt. Soc. Am. A. 27:977; Choi I. et al. (2011) "*Size-selective concentration and label-free characterization of protein aggregates using a Raman active nanofluidic device,*" Lab Chip. 11:632-8; Cho H. et al. (2009) "*Label-free and highly sensitive biomolecular detection using SERS and electrokinetic preconcentration,*" Lab Chip 9:3360-3363; Han B. et al. (2011) "*Application of silver-coated magnetic microspheres to a SERS-based optofluidic sensor,*" J. of Phys. Chem. C 115:6290-6296; Park S-M et al. (2009) "*A method for nanofluidic device prototyping using elastomeric collapse,*" Proc. Natl. Acad. Sci. 106:15549-15554). However, such microfluidic SERS devices introduce additional complexity to their fabrication, and may decrease sensitivity due to difficulties in the optical coupling, decreased sample volume, and the inability to concentrate the analyte by drying.

Various attempts have been made to translate the capabilities of SERS to a practical microsystem that can be utilized for routine analysis of samples in the lab or in the field (Liu G. L. and Lee L. P. (2005) Appl. Phys. Lett. 87:074101; Measor P. et al. (2007), supra, Appl. Phys. Lett. 90:211107; Strehle K. R. et al. (2007) "*A Reproducible Surface-Enhanced Raman Spectroscopy Approach. Online SERS Measurements in a Segmented Microfluidic System,*" J. Anal. Chem. 79:1542-1547; White I. M. et al. (2007) "*SERS-based detection in an optofluidic ring resonator platform,*" Optics Express 15(25):17433-17442; Quang L. X. et al. (2008) "*A portable surface-enhanced Raman scattering sensor integrated with a lab-on-a-chip for field analysis,*" Lab Chip 8:2214-2219; Choi D. et al. (2009) "*Additional amplifications of SERS via an optofluidic CD-based platform,*" Lab Chip 9:239-243; Gamby J. et al. (2009) "*Polycarbonate microchannel network with carpet of Gold NanoWires as SERS-active device,*" Lab Chip 9:1806-1808; Huh Y. S. et al. (2009), supra, Lab Chip 9:433-439; Wang G. et al. (2009) "*Surface-enhanced Raman scattering in nanoliter droplets: towards high-sensitivity detection of mercury (II) ions,*" J. Anal. Bioanal. Chem. 394:1827-1832; Wang M. et al. (2009) 6:411-417; Lim C. et al. (2010), supra, J. Analyst 135:837-844). In general, such SERS systems require microfabrication, and in some cases require nanofabrication to produce a surface with a metal nanostructure. As a result, chemical and biomolecular detection using SERS has been costly on a per-sample basis. Furthermore, SERS-active substrates produced through such conventional techniques have a short shelf life and must be used quickly. SERS activity of silver nanostructures has been shown to decrease drastically as a result of oxidation within a week (e.g., see Erol et al (2009), supra, J. Am. Chem. Soc. 131:7480-7481; Qi H. et al. (2010) "*The effect of size and size distribution on the oxidation kinetics and plasmonics of nanoscale Ag particles,*" Nanotechnology 21:215706). Thus, such conventional SERS systems have not been found practical for routine laboratory analysis of chemicals and biomolecules, and are not an option for field-based applications. Conventional SERS methodologies are therefore limited to laboratory settings due to their high cost and short shelf life.

Thus, there is a need for a relatively simple and low-cost SERS analytical system which overcomes some or all of the above-noted problems.

SUMMARY OF THE INVENTION

A novel, ultra low-cost surface enhanced Raman spectroscopy (SERS) analytical device has been developed by depositing (e.g. inkjet printing) plasmonic nanostructures into porous substrates (e.g. cellulose paper), which can be further modified to form hydrophobic and/or hydrophilic regions for fluidic operations such as analyte collection, separation and concentration.

The disclosed methods of SERS substrate fabrication and applications substantially reduce the high cost of nanofabricated substrates and microfabricated devices, while increasing the sensitivity and sophistication of SERS-based analytics. This new paradigm represents a significant advancement in on-site analytics, making SERS much more accessible in terms of cost and usability.

A SERS analytical device according to the present invention includes a porous substrate having regions of hydrophobicity, hydrophilicity, or combinations of both, for the purpose of collecting, separating, and concentrating analytes, and a plurality of plasmonic nanoparticles embedding in said porous substrate and forming a sensing region.

A method of fabricating a SERS analytical device according to a disclosed embodiment comprises the steps of: providing a porous substrate; modifying the substrate to form regions of hydrophilicity and/or regions of hydrophobicity; and embedding a plurality of plasmonic nanoparticles in the porous substrate, thereby forming a SERS sensing region.

According to one implementation of the present invention, a paper SERS analytical device is disclosed. An inexpensive consumer inkjet printer is utilized to modify cellulose paper substrates to be hydrophobic in a sensing region(s) with a sizing agent, such as for example a sizing agent comprising hexadecenyl succinic anhydride. Synthesized silver or other plasmonic nanoparticles are printed onto the hydrophobic sensing region(s) of the paper substrate with microscale precision to form sensing arrays. The hydrophobic surface prevents the aqueous sample from spreading throughout the paper and thus concentrates the analyte within the sensing region. For example, a SERS fingerprint signal for Rhodamine 6G dye was observed for samples with as low as 10 femtomoles of analyte in a total sample volume of 1 µL. This extraordinarily simple technique can be used to construct SERS microarrays immediately before sample analysis, enabling low-cost chemical and biomolecular detection in the lab as well as in the field at the point of sample collection.

The present invention is also directed to an implementation of the porous SERS analytical device in the form of SERS-active swabs or dipsticks, the SERS analytical device comprises hydrophilic cellulose paper, which forms or defines an analyte collection region. An inkjet printer is used to print the plasmonic nanoparticles such as silver or gold nanoparticles onto the cellulose paper to form a sensing region. The detection of 250 attomoles of Rhodamine 6G was demonstrated as an example using this inkjet fabricated SERS-active paper surface swab or dipstick. The fabrication simplicity and ease of use of this device is unprecedented for SERS-based analytics.

The present invention is also directed to an implementation of the porous SERS analytical device in a novel technique for trace chemical detection referred to herein as filter SERS. Filter SERS avoids the high costs of nanofabricated SERS substrates and the complexity associated with conventional microfluidic-based SERS by leveraging the filtration process to create a SERS active substrate and to concentrate the analyte. The membrane traps and concentrates nanoparticles (e.g., silver nanoparticles) from a colloid solution to form a SERS-active substrate through which a large volume of sample can be readily passed. Filter SERS allows large volumes of trace analyte samples to be processed very quickly, resulting in orders of magnitude increases in the number of analyte molecules that interact with the SERS-active surface as compared to conventional techniques. A significant improvement in detection limit is demonstrated, such as compared to colloidal SERS for the pesticide malathion and the food contaminant melamine. The measured SERS intensity exhibits low variation relative to traditional SERS techniques, and the data can be closely fit with a Langmuir isotherm. Due to the simple procedure, the low-cost of the substrates, the quantitative results, and the performance improvement due to analyte concentration, the disclosed techniques enable SERS to be practical for a broad range of analytical applications, including field-based detection of toxins in large-volume samples.

In one implementation of filter SERS, a kit for detecting a target analyte according to the present invention includes a solution comprising plasmonic nanoparticles (e.g., silver nanoparticles), a porous membrane configured to trap and concentrate the metal nanoparticles (the porous membrane can be formed from nylon, polyvinylidene fluoride (PVDF), paper, or other fibrous materials), and a membrane holder configured to retain the porous membrane and a syringe. The nanoparticle solution is first passed using the syringe through the porous membrane to form a SERS sensing region, the sample is then passed through the porous membrane upon actuation of the syringe, so that the target analyte, if present in the sample, is concentrated into the SERS sensing region.

A method of detecting a target analyte according to a disclosed embodiment comprises the steps of: providing a porous membrane having a SERS sensing matrix; collecting the target analyte from a sample by pipetting, wiping, dipping, soaking, or filtering, whereby the target analyte, if present in the sample, is further separated from the sample and concentrated in the SERS sensing matrix; and analyzing the substrate after the collection and concentration step using SERS detection equipment. The SERS detection equipment may include a spectrometer, an excitation source, and optics to condition and filter the excitation and collection light beam.

According to one embodiment of the present invention, a surface enhanced Raman spectroscopy (SERS) analytical device includes a substrate having a porous structure, and a plurality of plasmonic nanoparticles embedded in the porous structure and forming a sensing region. Preferably, the plasmonic nanoparticles do not entirely coat the surface of the substrate, but are rather embedded in discrete portions of the substrate. In some implementations, the substrate is formed from cellulose, modified cellulose, a natural polymer, an artificial polymer, glass fibers, a metal, or combinations thereof. For example, materials may be blended and/or otherwise combined or layered utilizing two or more materials including a porous morphology. In some embodiments, the substrate includes at least one of a hydrophilic portion or a hydrophobic portion.

In one implementation, the plurality of plasmonic nanoparticles includes one or more clusters of nanoparticles. Multiple clusters may be provided, wherein one of the clusters is spaced from and discretely disposed relative to another of the clusters. In another implementation, the plurality of plasmonic nanoparticles includes a plurality of individual nanoparticles each of which are spaced from and discretely disposed relative to other of the nanoparticles. The plasmonic nanoparticles may be formed from various materials, such as for example silver, gold, copper, platinum, combinations thereof, or other SERS active materials.

A method of fabricating a surface enhanced Raman spectroscopy (SERS) device according to an embodiment of the present invention comprises the steps of: providing a substrate having a porous morphology; and embedding a plurality of plasmonic nanoparticles in the porous substrate, thereby forming a SERS sensing region.

In one embodiment, the method of fabricating includes the further step of modifying at least a portion of the substrate to form a hydrophobic region or a hydrophilic region. In one implementation, the modifying step includes coating at least a portion of the substrate with a substance to form the hydrophobic region or the hydrophilic region. Coating the portion of the substrate may be effectuated via various processes, such screen printing, inkjet printing, spraying, pipetting, or soaking.

In another embodiment, the embedding step of the disclosed method includes the steps of providing a nanoparticle ink solution containing the plurality of plasmonic nanoparticles; and depositing the nanoparticle ink solution onto the substrate. In some implementations, the nanoparticle ink solution comprises a modifier for controlling the viscosity and/or the surface tension of the nanoparticle ink solution. In some implementations, the nanoparticle ink solution comprises a modifier for controlling aggregation, oxidation, or stability of the plasmonic nanoparticles in the nanoparticle ink solution. In some implementations, the depositing step is achieved via inkjet printing, screen printing, stamping, spraying, micro-pipetting, filtering, or soaking.

In one embodiment, a single SERS sensing region is formed at a selected position on the substrate during the embedding step. In other embodiments, an array of SERS sensing regions is formed at a selected position on the substrate during the embedding step. The array may include a selected pattern of discrete SERS sensing regions.

A method of detecting a target analyte in a sample according to an embodiment of the present invention includes the steps of: providing a porous membrane having a surface enhanced Raman spectroscopy (SERS) sensing matrix; contacting the sample with the porous membrane, whereby the target analyte, if present in the sample, is concentrated in the SERS sensing matrix; and analyzing the porous membrane after the contacting step using SERS detection equipment.

According to embodiments of the disclosed invention, the contacting step of the method of detection includes pipetting the sample onto the porous membrane, passing the sample through the porous membrane, swabbing the porous membrane over a surface containing the sample, or dipping the porous membrane into the sample. According to one embodiment, the disclosed method includes the further step of dipping the porous membrane into a solvent, thereby concentrating via lateral flow the target analyte, if present in the sample.

In one embodiment, the disclosed method of detection includes the further steps of: providing a colloid solution comprising plasmonic nanoparticles; and trapping the plasmonic nanoparticles from the colloid solution in the porous membrane to form the SERS sensing matrix.

According to embodiments of the present invention, the porous membrane is formed from a material selected from the group of nylon, polyvinylidene fluoride (PVDF), cellulose, modified cellulose, a natural polymer, a synthetic polymer, glass fibers, a metal, or combinations thereof. Other suitable materials having a porous morphology may also be utilized.

A kit for detecting a target analyte according to an embodiment of the present invention includes a solution comprising plasmonic nanoparticles, a porous membrane configured to trap and concentrate the plasmonic nanoparticles when the solution passes through the porous membrane to form a surface enhanced Raman spectroscopy (SERS) sensing region, a containing device configured to hold a sample being tested for target analyte, and a membrane holder configured to retain the porous membrane. The sample in the containing device is passable through the porous membrane so that the target analyte, if present in the sample, is concentrated in the SERS sensing region.

According to one embodiment, the containing device of the kit is additionally configured to hold the solution. The solution is passable through the porous membrane to form the SERS sensing region.

BRIEF DESCRIPTION OF THE DRAWINGS

FIG. 3A illustrates signals acquired from 10 femtomoles of R6G in the droplet sample; FIG. 3B illustrates signals acquired from 100 femtomoles of R6G in the droplet sample; FIG. 3C illustrates signals acquired from 1000 femtomoles of R6G in the droplet sample. A 5-point Fast-Fourier Transform (FFT) smoothing is used on the data.

FIG. 8A depicts a comparison of R6G detection performance of filter SERS with a sample in colloid dried onto a surface. FIG. 8B depicts Raman spectra data for a range of R6G concentrations using filter SERS, with dilutions of R6G in water from 100 µM down to 10 nM. FIG. 8C depicts a plot of the intensity of the 1509 cm$^{-1}$ R6G Raman peak for various R6G concentrations using nylon and PVDF membranes. Each data set is fit with a Langmuir isotherm.

FIG. 10A depicts a comparison of melamine detection performance of filter SERS with a sample in colloid dried onto a surface. FIG. 10B depicts Raman spectra data for melamine detected using filter SERS. FIG. 10C depicts a plot of the intensity of the 690 cm$^{-1}$ melamine Raman peak for various melamine concentrations. The data is fit with a Langmuir isotherm.

FIG. 11A depicts a comparison of malathion detection performance of filter SERS with a sample in colloid dried onto a surface. FIG. 11B depicts Raman spectra data for malathion detected using filter SERS. FIG. 11C depicts a plot of the intensity of the 508 cm$^{-1}$ malathion Raman peak for various malathion concentrations. The data is fit with a Langmuir isotherm.

DETAILED DESCRIPTION OF THE INVENTION

The present invention is directed to a porous SERS analytical device suitable for molecular analysis via surface enhanced Raman spectroscopy (SERS). The present invention provides for an inexpensive yet highly sensitive SERS device, which is fabricated from a porous substrate designed with regions of hydrophobicity, hydrophilicity, or combinations of both, for the purpose of collecting, separating, and concentrating analytes, and a plurality of plasmonic nanoparticles embedding in said porous substrate forming a sensing region.

According to one embodiment, a SERS microdevice comprises a substrate having a hydrophobic region, and a plurality of plasmonic nanoparticles embedded in the hydrophobic region, thereby forming a sensing region. The plasmonic nanoparticles are preferably noble metal nanoparticles, such as silver or gold nanoparticles. The metal nanoparticles may be embedded into the substrate with any desired pattern with microscale precision using an inkjet printer. Thus, an array of SERS sensing regions may be printed onto the substrate, wherein the array includes a selected pattern of discrete SERS sensing regions.

The porous substrate may be formed from a fibrous material, such as cellulose paper. The inkjet printer may be used to modify all or a portion of the paper (or other substrate) to create a hydrophobic region on the paper, which prevents the sample being tested from spreading. For example, all or a portion of the surface of the paper may be coated with a sizing agent, such as hexadecenyl succinic anhydride. The sizing agent may be applied via an inkjet printer, thereby further simplifying the fabrication process. The plasmonic nanoparticles are then embedded (e.g., via inkjet printing a solution specially formulated of nanoparticle ink) onto the hydrophobic region of the paper to form the SERS sensing region. Any analyte molecules in the sample are concentrated in the sensing area.

SERS measurements may be acquired by placing a sample droplet onto the SERS sensing region. The fingerprint signal of a particular analyte may be identified with a relatively small concentration of analyte (e.g., 10 femtomoles or less) applied to the sensing region of the paper-based SERS substrate. A sensing region with micron-size resolution may be readily formed on a paper substrate via inkjet printing. Further, an array of discrete sensing regions may be formed to provide a selected matrix of sensing regions.

Figure 12:
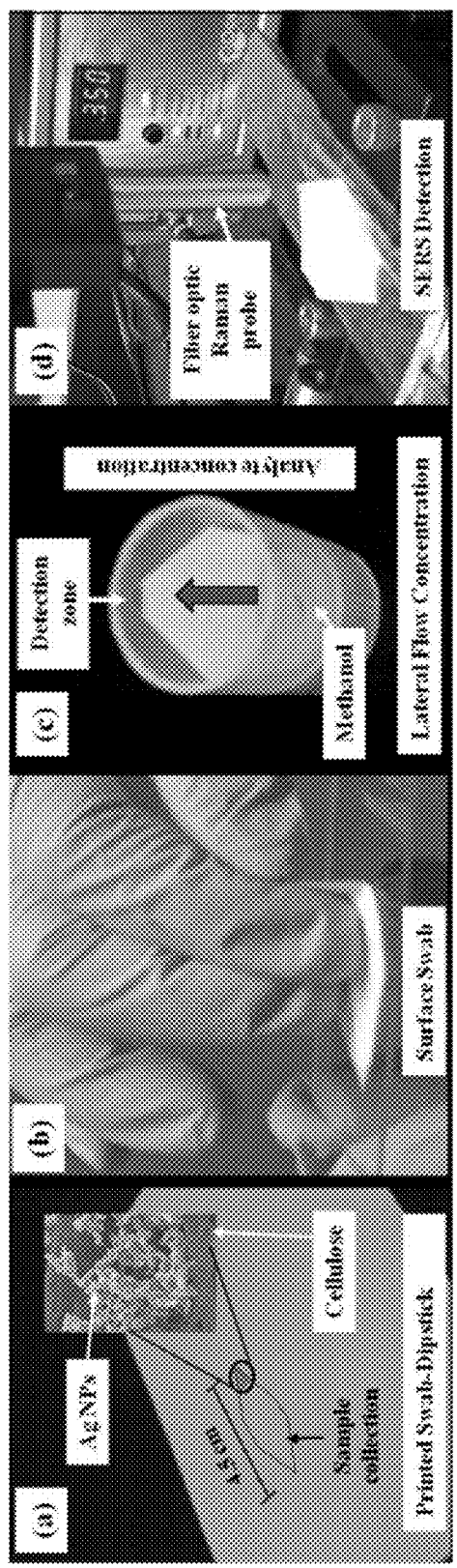
FIGS. 12a, 12b, 12c and 12d illustrate a method of fabricating and using an inkjet-printed SERS-active paper swab dipstick. Ag NPs are printed onto paper to form swab-dipsticks (FIG. 12a, with the inset showing SEM of Ag NPs on an exploded portion of the paper). A surface is then swabbed with the swab-dipstick (FIG. 12b). Lateral flow concentration is achieved by placing the swab-dipstick in a vial of methanol (FIG. 12c). The SERS signal is detected using a portable spectrometer using a fiber optic Raman probe (FIG. 12d).

According to another embodiment, an inkjet-printed SERS-active paper swab dipstick is disclosed, such as shown in FIG. 12. A portion of the substrate includes a sensing region having one or more clusters of metal (e.g., silver) nanoparticles, as described above. The remaining portion of the substrate is usable as a swab to pick up trace analytes from a surface, and as a dipstick with lateral flow concentration of the collected analyte into the detection volume. In the case of a surface swab, the SERS-active paper is simply wiped over a surface to collect the analyte. Alternatively, in the case of liquid sample testing, the SERS-active paper is dipped into the sample. The capillary action of the cellulose fibers wicks the sample into the paper, including any target analyte present. Thus, the portion of the paper usable as a swab or dipped into the sample is preferably hydrophilic, and defines or forms an analyte collection region.

After either of these sample collection procedures (swabbing or dipping), the SERS-active paper swab dipstick is placed in a vial containing a solvent, as shown in FIG. 12c. As the solvent is wicked up the paper, it carries analyte molecules from the sample up to the tip of the dipstick and sensing region. As demonstrated herein, the detection of as few as 250 attomoles of analyte molecules concentrated into a square millimeter-sized area is achieved utilizing only the microcapillary action of the paper. As such, this device requires no syringe pumps, generation of electric fields, microfabrication, or external equipment of any kind to load and concentrate analyte molecules in the sensing region, making it a uniquely simple optofluidic SERS assay. In addition, the technique is demonstrated to be quantitative and has fairly low signal variability.

The SERS-active paper swab dipstick has applications as a surface swab for explosives or pesticide testing, and as a dipstick for liquid sample testing. Additionally, by bio-functionalizing the device, point-of care bio-assays may be fabricated.

Figure 5:
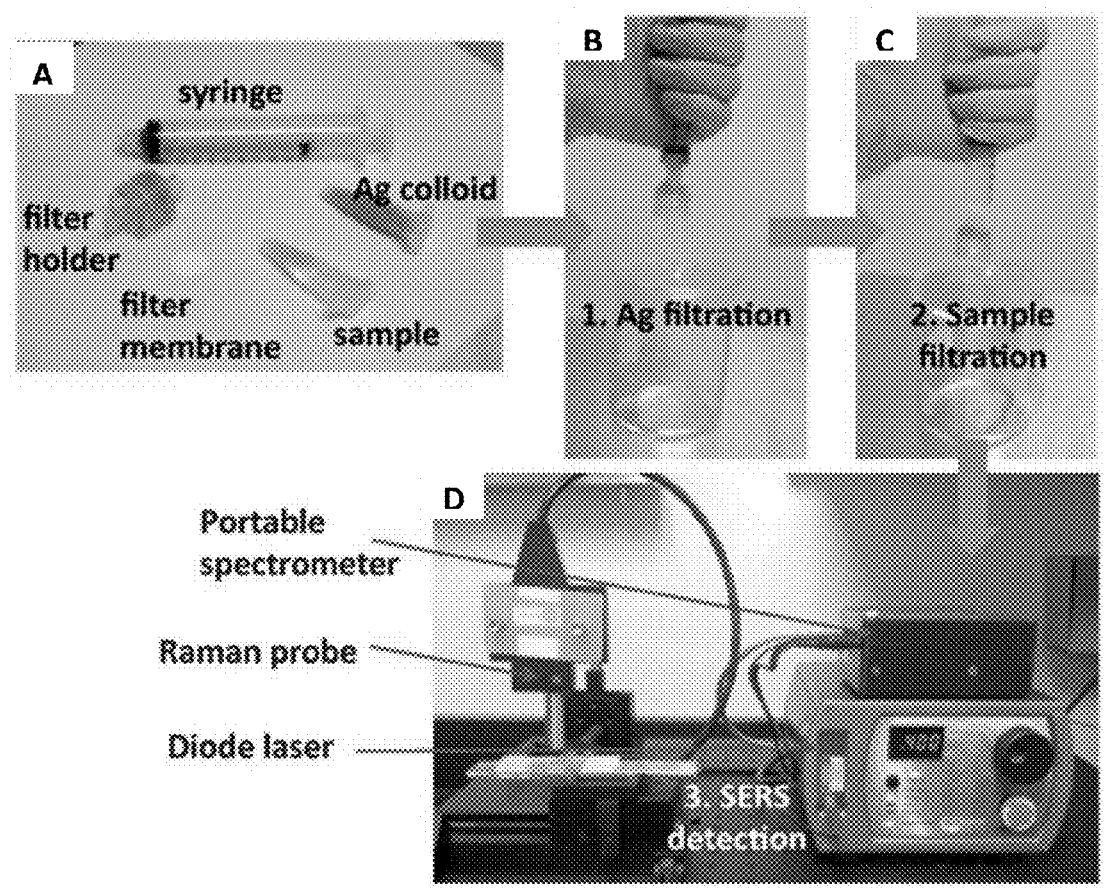
FIG. 5A illustrates filter SERS Assay kit components and a method of detecting analyte according to embodiments of the present invention.
Referring to FIGS. 5B, 5C and 5D, a SERS-active substrate may be created by passing a silver colloid solution through a filter membrane using a syringe (FIG. 5B). Analyte molecules are concentrated into the substrate from a large sample volume (FIG. 5C). The SERS signal is then detected using a small and portable photonic setup (FIG. 5D).

According to another embodiment, the present invention relates to a kit for detecting a target analyte (FIG. 5). The kit includes a solution comprising plasmonic nanoparticles (e.g., silver or gold nanoparticles), a porous filter membrane, a membrane holder, and a syringe.

The porous membrane is configured to trap and concentrate the nanoparticles when the solution passes through the porous membrane to form a SERS sensing region. Suitable filter membranes include nylon and polyvinylidene fluoride (PVDF) filter membranes, as well as porous membranes formed from fibrous materials (e.g., cellulose, glass fibers and other natural and synthetic polymer materials). The specific pore size and material composition of the porous membrane may vary depending on the particular size and composition of the nanoparticles, as well as the particular target analyte to enhance the performance of the SERS device.

The SERS sensing region may conveniently and readily be formed by loading the nanoparticle solution into the syringe, attaching a new porous membrane to the syringe via the membrane holder, and then passing the solution through the membrane (via actuation of the syringe). As the nanoparticle solution passes through the filter membrane, the nanoparticles are trapped and concentrated in a discrete portion of the membrane, thereby forming the SERS sensing region.

After preparing or forming the SERS sensing region on the filter membrane, the syringe is removed from the filter membrane holder. The syringe may then be loaded with a volume sample to be tested, and re-attached to the filter membrane holder (containing the filter membrane with SERS sensing region). The sample being tested for the target analyte is then passed through the filter membrane. The target analyte, if present in the sample, is concentrated in the SERS sensing region or matrix.

Following the collection and concentration of the target analytes by pipetting, soaking, dipping, swabbing, filter or other methods, the SERS active porous substrate containing the concentrated analytes is analyzed using SERS detection equipment, which may include a portable spectrometer, an excitation source (e.g., a diode laser), and optics to condition and filter the excitation and collection light beam.

Having generally described the invention, the same will be more readily understood through reference to the following examples, which are provided by way of illustration and are not intended to be limiting of the present invention unless specified.

EXAMPLES

Example 1

Materials

Fisherbrand chromatography paper, 0.19 mm in thickness, was used for the substrate. Hexadecenyl succinic anhydride (ASA) from Thermo-Fisher Scientific (Pittsburgh, Pa.) was used to create a hydrophobic surface on the paper. Silver nitrate, sodium citrate, glycerol, and hexanol were obtained from Sigma-Aldrich (St. Louis, Mo.). Rhodamine 590 chloride, also known as Rhodamine 6G (R6G), was purchased from Exciton (Dayton, Ohio).

Nanoparticle Synthesis

Silver nanoparticles were synthesized using the method of Lee and Meisel (Lee P. C. and Meisel D. (1982) J. Phys. Chem. 86:3391-3395). Briefly, 90 mg of silver nitrate was added to 500 mL of ultrapure water (18.2 M$\Omega$), which was then brought to a boil in a flask under vigorous stirring. Sodium citrate (100 mg) was added, and the solution was left to boil for an additional 10 min. After the solution turned greenish brown, which indicated the formation of silver colloid, it was then removed from the heat.

Printing

An Epson Workforce 30 inkjet printer was chosen to generate the SERS-active substrates. Prior to the printing of silver nanoparticles onto paper, the substrate was made hydrophobic using ASA, a common paper sizing agent. Hydrophobization was achieved by inkjet printing a 10% ASA solution in hexanol onto the entire surface of the paper, followed by curing at 175° C. on a laboratory hot plate for 5 min.

To form the silver ink, nanoparticle colloids (described above) were centrifuged at 10000 g to concentrate the nanoparticles. 98% of the supernatant was removed, and glycerol in a volume ratio of 2:5 (glycerol/colloid solution) was added to the remaining solution to adjust the viscosity and surface tension of the ink for optimal printing. To prevent clogging of the print head, the nanoparticle ink was filtered using a 0.2 $\mu$m Millipore PTFE membrane filter to remove any large particles from the ink solution.

The ink was then injected into refillable printing cartridges. An open source vector graphics editor, Inkscape, was used to define the shapes to print using colors that correspond to unique cartridges. Silver nanoparticles were printed in circles of about 1 mm diameter. To increase the nanoparticle concentration in the paper, the printing of sensors was repeated five times.

SERS Measurements

Measurements were acquired within 3 hours of printing the substrates. SERS was performed using a Horiba Jobin-Yvon LabRAM HR-VIS Raman microscope using 632.8 nm HeNe laser excitation with less than 15 mW output. A 10× objective was used for focusing the excitation light onto the substrate and for collecting the scattered photons. The paper containing an array of printed SERS active regions was taped onto a glass slide, which was then placed on the microscope stage. Using a micropipet, a 1 $\mu$L droplet of sample analyte was placed onto the printed circle of silver nanoparticles. SERS measurements were acquired after the droplet dried. Concentrations of 1 nM, 10 nM, 100 nM, and 1 $\mu$M R6G in water were tested on three spots each. Measurements were acquired at three different locations within each printed circle, giving a total of nine SERS measurements for each R6G concentration. For 1 nM and 10 nM concentrations, a 5 s CCD exposure was used; for 100 nM R6G, a 2 s exposure was used, and for 1 $\mu$M, a 2 s exposure and an optical density 1 (OD1) filter on the laser were used. To determine the SERS enhancement factor of the inkjet-printed substrates, a 1 $\mu$L droplet of 2 mM R6G was spotted onto paper coated with ASA. The resulting signal was compared with the SERS measurements recorded with printed silver spots; for each recorded signal, the area within two prominent R6G Raman bands was integrated, and the resulting value was compared between the SERS-active and non-SERS active substrates.

Results and Discussion

When an organic material is used as a SERS substrate, one must be concerned that the scattered light from the substrate could overwhelm the signal from the analyte. In fact, we measured the scattered light from 21 different types of paper in order to select the material with the least background signal. These materials included printer paper, 100% cotton fiber paper, coffee filter paper, a napkin, and many others. The Raman microscope was used to measure the scattered light detected within the spectrum of interest for SERS detection (500-2000 cm$^{-1}$). The signal from many of the papers saturated the CCD of the spectrometer after only a few seconds of integration time, making them difficult to use for paper-based SERS. This is likely due to the chemical treatments that some paper products undergo (e.g, see Pelton R. (2009), supra, Trends Anal. Chem. 28:925-942). The papers with the lowest background were filter paper and chromatography paper, which contain primarily cellulose. Chromatography paper was utilized for the SERS measurements.

Figure 1:
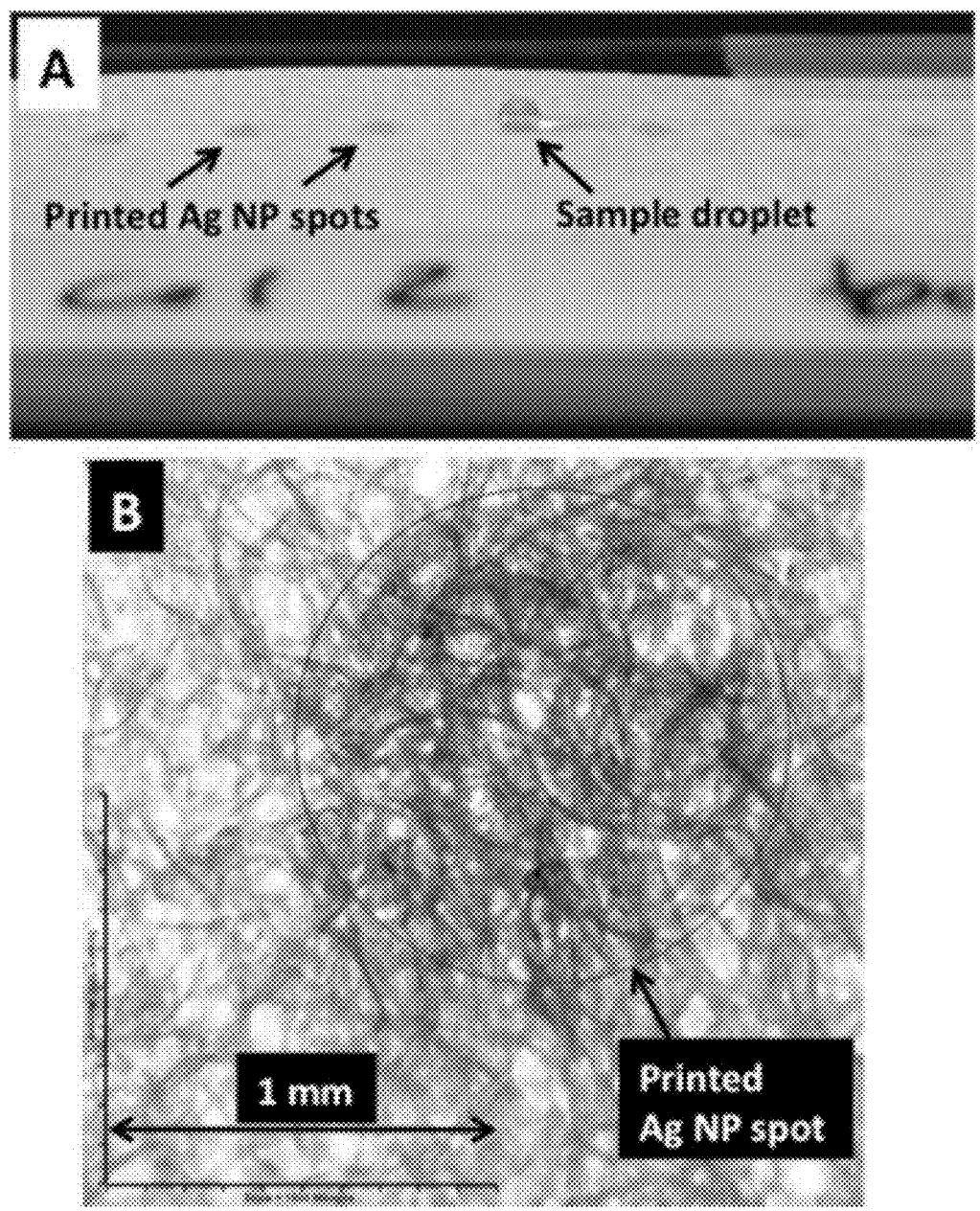
FIG. 1A is an image of an array of inkjet-printed silver nanoparticle (Ag NP) spots on chromatography paper, and showing a 1 µL aqueous sample droplet placed on one of the printed Ag NP spots.
FIG. 1B is a micrograph image of one printed Ag NP spot on paper in bright-field mode.

FIG. 1A shows an image of silver nanoparticles printed onto the paper. The circles of printed nanoparticles were designed to be 1 mm in diameter. During printing, the silver nanoparticles appear brown on the paper initially and progressively become darker in color with each consecutive printing. Upon drying, the spots appear grayish due to the formation of silver clusters. For all of the SERS measurements, five printing cycles of nanoparticles were used. With regard to the number of print cycles, it was observed that multiple print cycles resulted in increased SERS activity as compared to a single print cycle. However, the synthesis of the silver nanoparticle ink could be optimized to minimize the need for multiple print cycles.

The precision with which the nanoparticle array was printed is demonstrated in FIG. 1B, which is a magnified image of one of the nanoparticle substrates in FIG. 1A. Even after five printing cycles, the transition between the silver nanoparticle embedded region and the region without silver is clearly distinguishable. It appears that even with repeated feeds, printing with a precision better than tens of micrometers was achieved. With alternative ink formulations, repeated printing may be avoided. Precision printing of 10 μm and lower is permissible using higher precision printers. As such, it is possible to print SERS microarrays with sub-millimeter sensor sizes via the methods disclosed herein.

Printing high-precision, small-area SERS-active substrates on paper is not useful if the sample delivery is not well controlled. We observed that a 1 μL droplet of water applied to plain chromatography paper immediately spreads by approximately 5 mm in diameter, which dilutes the sample across this large area. For SERS, this is problematic, as the laser excitation is delivered only to a sub-millimeter area of the sensor. To control the aqueous sample delivery, we first inkjet-printed ASA, a common paper sizing agent, onto the sensing region of the paper before printing the nanoparticles. As seen in FIG. 1A, when a 1 μL droplet of water is applied to the SERS-active spot, the water beads up on top of the biosensor, slowly drying in place. This delivers all of the target analyte molecules onto the small-area SERS-active substrate. The simplicity of this inkjet printing hydrophobization technique means that the paper can be treated immediately before use as a sensing substrate.

Figure 2:
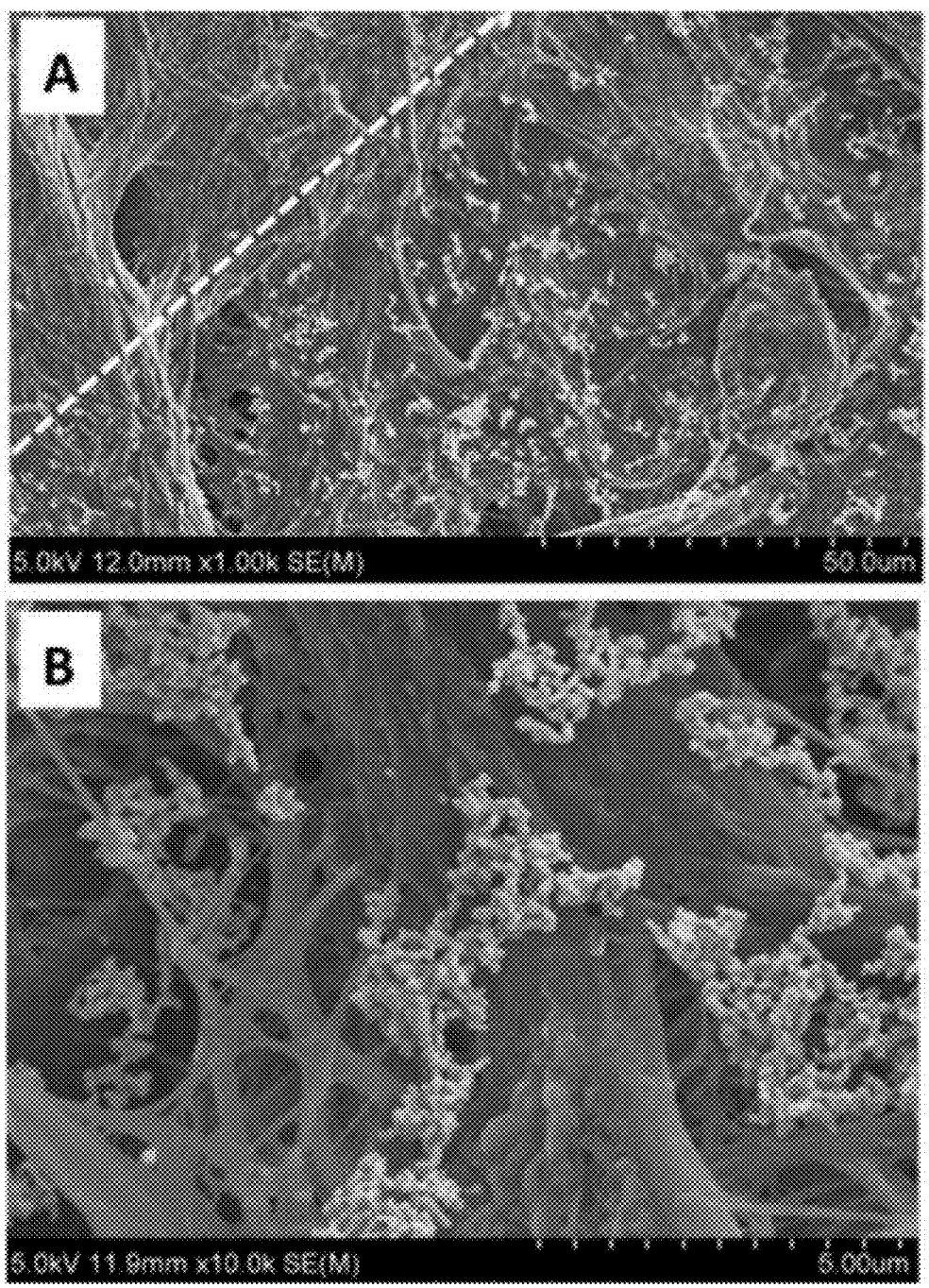
FIG. 2A is a scanning electron micrograph (SEM) image of a printed Ag NP spot, wherein the dashed line shows the boundary of the spot (or NP clusters).
FIG. 2B is a SEM image of the printed Ag nanoclusters of FIG. 2A within the printed spot.

FIG. 2 shows a scanning electron micrograph of silver nanoparticle clusters from one of the inkjet-printed spots on paper. The high surface density of silver nanoclusters shown in FIG. 2A illustrates the promise of this printing technique for generating substrates with high SERS activity. The image also reveals the precision of the inkjet-printing technique. The dashed line shows the discrete border of the printed SERS-active spot. The density of silver nanoclusters below and to the right of the dashed line is similar throughout the entire spot, while it is essentially zero to the upper left of the dashed line. FIG. 2B shows a few selected silver nanoclusters dried onto the paper fibers. These clusters, which assemble as the silver colloid solution dries, are advantageous for many SERS applications, as they cause the localized surface plasmon resonance to extend into the red and infrared and also generate higher SERS enhancements due to hot spots.

Figure 3:
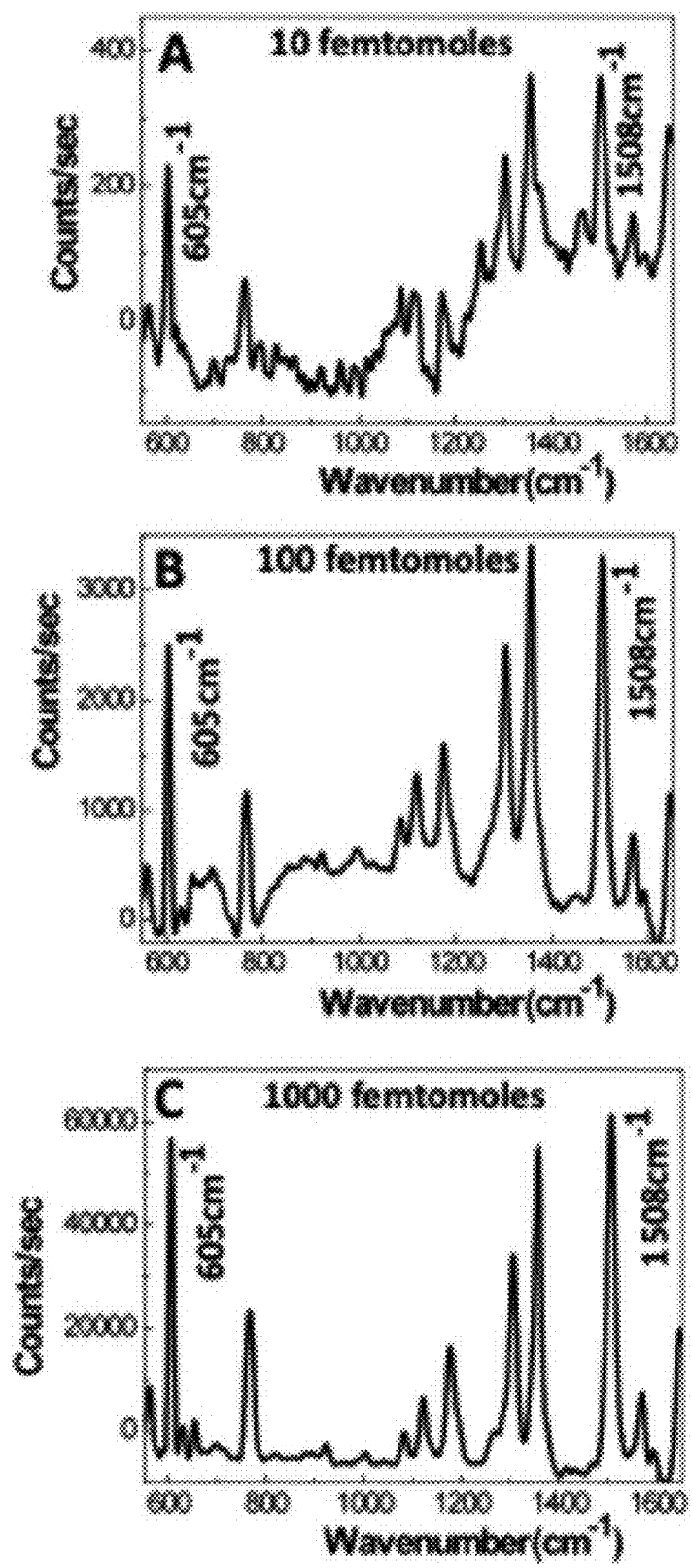
FIGS. 3A, 3B and 3C are graphs illustrating typical Raman spectra of R6G acquired from three spots on a printed array.

Typical SERS signals recorded for 10, 100, and 1000 nM R6G concentrations are shown in FIG. 3. As only 1 μL sample volume is consumed for each measurement, the total number of R6G molecules applied to the sensors is 10, 100, and 1000 femtomoles, respectively. Different CCD exposure times and laser power values were used to record the SERS signals across the concentration range shown in FIG. 3; the signals are normalized to 1 s of CCD exposure and to zero optical density filtering of the laser source. Even for the signal acquired from 10 femtomoles of analyte, the characteristic R6G Raman bands at 605, 1310, 1365, and 1508 cm$^{-1}$ have high signal-to-noise ratio and are easily distinguishable. As a result of the extended exposure time (5 s) for this concentration, optical scattering due to the paper is also visible; however, it does not interfere with the ability to identify the R6G Raman signal. The high signal-to-noise ratio for these R6G Raman bands indicates that we can detect a relatively low concentration of analyte.

The SERS enhancement factor for the inkjet-printed substrate was determined by comparing signals acquired on paper with and without printed silver nanoparticles. For a 1 μL droplet of 2 mM R6G on paper, the acquired SERS signal (N=3) for the 1508 cm$^{-1}$ was approximately equal to the signal acquired for 10 nM R6G on the printed silver nanoparticles. This implies an enhancement factor of $2\times10^5$. Considering that the silver nanoclusters cover only approximately 5% of the surface (FIG. 2), the average enhancement factor of individual nanoclusters is nearly $10^7$, which is a typical enhancement factor for nanoclusters under red excitation. Nanoparticle geometry and clustering may be further optimized for peak resonance at the Raman excitation wavelength. Combining this with increased nanocluster density, the SERS enhancement for the inkjet-printed substrates can approach $10^7$, which is in the range of many micro/nanofabricated SERS substrates (see Lin X-M et al. (2009) "*Surface-enhanced Raman spectroscopy: substrate-related issues*," Anal. Bioanal. Chem. 394:1729-1745).

Variation in measured signal intensity across various locations has always been a concern for SERS, especially when the substrate has randomized features. To determine if signal inconsistencies pose problems for our inkjet-printed SERS substrates, we recorded SERS signals from three randomly selected locations within each printed SERS-active spot, separated by a distance greater than 100 μm, and we recorded signals from three printed spots for each concentration of R6G (i.e., nine data sets for each sample concentration). To analyze the collected signals, we calculated the area in the 605 and 1508 cm$^{-1}$ R6G Raman bands and then summed the areas for each acquired signal (after normalization). Table 1 shows the mean and standard deviation of the sums within each SERS-active spot in the array. The results indicate that the variation within each spot is small, but variation from spot to spot for the same concentration is relatively large. We suspect that this resulted from a combination of factors: namely, the random clustering of the silver nanoparticles, variations in printing process, and inconsistency in applying the 1 μL sample droplet onto each spot.

TABLE 1

Mean and Standard Deviation of Sum of the Integrals of the 605 and 1508 cm$^{-1}$ R6G Raman Bands within Each SERS-Active Spot in the Array

| Concentration of R6G (nM) | Spot No. | Mean No. of Counts/s | Standard Deviation |
| --- | --- | --- | --- |
| 10 | 1 | $1.07 \times 10^4$ | $2.07 \times 10^3$ |
|  | 2 | $8.28 \times 10^3$ | $6.36 \times 10^2$ |
|  | 3 | $4.04 \times 10^3$ | $5.28 \times 10^2$ |
| 100 | 4 | $7.47 \times 10^4$ | $9.92 \times 10^3$ |
|  | 5 | $3.15 \times 10^4$ | $1.54 \times 10^4$ |
|  | 6 | $9.44 \times 10^4$ | $1.90 \times 10^4$ |
| 1000 | 7 | $2.98 \times 10^6$ | $1.30 \times 10^6$ |
|  | 8 | $3.31 \times 10^6$ | $9.62 \times 10^5$ |
|  | 9 | $2.38 \times 10^6$ | $2.11 \times 10^6$ |

Figure 4:
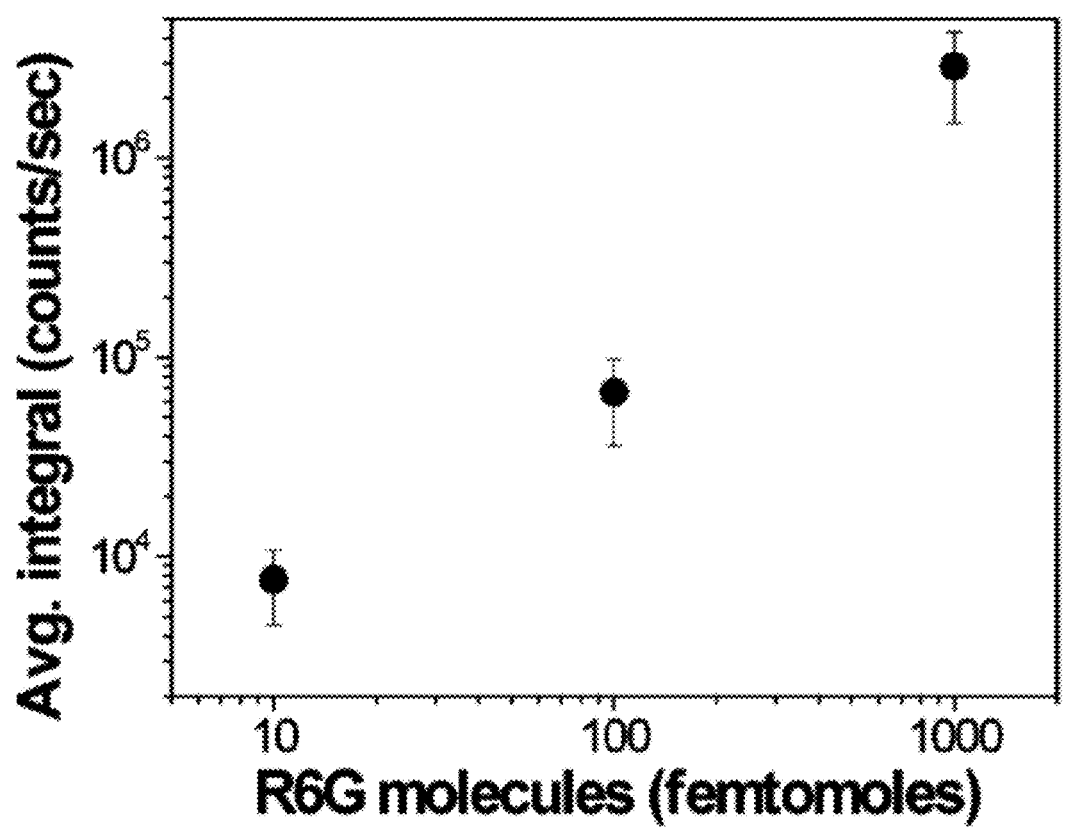
FIG. 4 is a graph illustrating average signal magnitude and standard deviation for each R6G concentration (10, 100 and 1000 femtomoles). For each concentration, three signals are acquired from each of three spots. The data points represent the averaged sum of the integrals of the 605 and 1508 cm$^{-1}$ R6G Raman bands.

However, when analyzing the signal for each concentration across the respective three spots, a predictable trend in the data emerges. In FIG. 4, we have plotted the mean and standard deviation across all of the nine signals acquired for each concentration (three signals acquired at three locations in each of three spots). These results illustrate that overall the measurements are repeatable and predictable across the concentration range using an inkjet-printed array of SERS-active sensors.

Thus, we have demonstrated an ultra-low-cost, paper-based SERS substrate using inkjet printing as the fabrication method. A high signal-to-noise ratio was achieved, even with as little as 10 femtomoles of analyte molecules in the entire sample volume and with a relatively low power, red laser as the excitation source. In addition to the excellent performance, the substrate does not require any complicated or lengthy micro- or nanofabrication. The SERS substrate can be created in nearly any environment at the moment the user is ready to perform a measurement, thereby eliminating the problem of the limited shelf life of SERS substrates because the inkjet-printed substrates do not need to be acquired in bulk and stored. Instead, the SERS microdevices may be fabricated with unprecedented simplicity and speed at the time and point of use.

The extremely low cost and simplicity of fabrication make the paper-based SERS substrates ideal for a number of applications, including routine lab use, as well as use in the field at the point of sample acquisition. Additional variations of the disclosed techniques include integration with paper-based microfluidics and the use of a simple fiber optic probe to excite the substrate and collect the scattered light when performing measurements. Such a technique has the potential to dramatically increase the applicability of SERS-based chemical and biomolecular detection and, as a result, enable much-needed low-cost and rapid sample analysis.

Example 2

We demonstrate the detection performance of the filter SERS technique of at least 1-2 orders of magnitude better than the typical approach of drying a sample in silver colloid onto a surface. We achieved a detection limit of 10 nM for the common model SERS analyte Rhodamine 6G (R6G) using a portable spectrometer and diode laser. Furthermore, we demonstrate the utility of the filter SERS technique for field based applications by detecting parts per billion (ppb) concentrations of melamine, a food contaminant, as well as ppb concentrations of malathion, a widely used pesticide, in aqueous solution. The disclosed technique shows relatively low variability, and all acquired data sets could be fit well with a Langmuir isotherm. This indicates that the disclosed field based technique is not only simple and sensitive, but it can also be quantitative.

Materials

Nylon and Millipore PVDF filter membranes, 13 mm diameter, 0.22 μm pore sizes were purchased from Fisher Scientific (Pittsburgh, Pa.) and used with syringe filter holders from Cole-Palmer (Vernon Hills, Ill.) for performing the filter SERS assay. Silver nitrate, sodium citrate, sodium chloride and melamine were obtained from Sigma-Aldrich (St. Louis, Mo.). R6G was purchased from Exciton (Dayton, Ohio). Malathion was purchased from Cerilliant (Round Rock, Tex.).

Nanoparticle Synthesis

Silver nanoparticles were synthesized by the method of Lee and Meisel (Lee P. C. and Meisel D. (1982), supra, J. Phys. Chem. 86:3391-3395). Briefly, 90 mg of silver nitrate was added to 500 mL of ultrapure water (18.2 ΩU), which was then brought to a boil in a flask under vigorous stirring. Sodium citrate (100 mg) was added, and the solution was left to boil for an additional 10 min. After the solution turned greenish brown, which indicated the formation of silver colloid, it was removed from heat. Silver nanoparticles are aggregated using 5 mM NaCl, as it was experimentally determined that this provided the optimal level of clustering.

Filter SERS Assay

Filter SERS Assay components are illustrated in FIG. 5A. To perform the filter SERS assay, the filter membrane is first wetted by dipping it in a 50% ethanol-water mixture. The membrane is then placed into the filter holder, which can be attached to a typical syringe. A volume of silver colloid solution is loaded into the syringe. The filter holder is then attached to the syringe and silver colloid is passed through the filter membrane, as shown in FIG. 5B. The membrane traps the silver nanoparticles, forming a SERS active substrate.

The filter holder is removed, and the same syringe is then loaded with the sample. After re-attaching the filter holder, which now contains the nanoparticle-coated membrane, the sample is passed through the membrane, as shown in FIG. 5C. Target analyte molecules become adsorbed onto the nanoparticles or to the filter membrane, effectively concentrating the analyte. The membrane is then removed from the holder, dried, and analyzed using a SERS detection setup consisting of a portable spectrometer (Ocean Optics QE65000), a 785 nm diode laser, and a fiber optic Raman probe, as shown in FIG. 5D.

Figure 6:
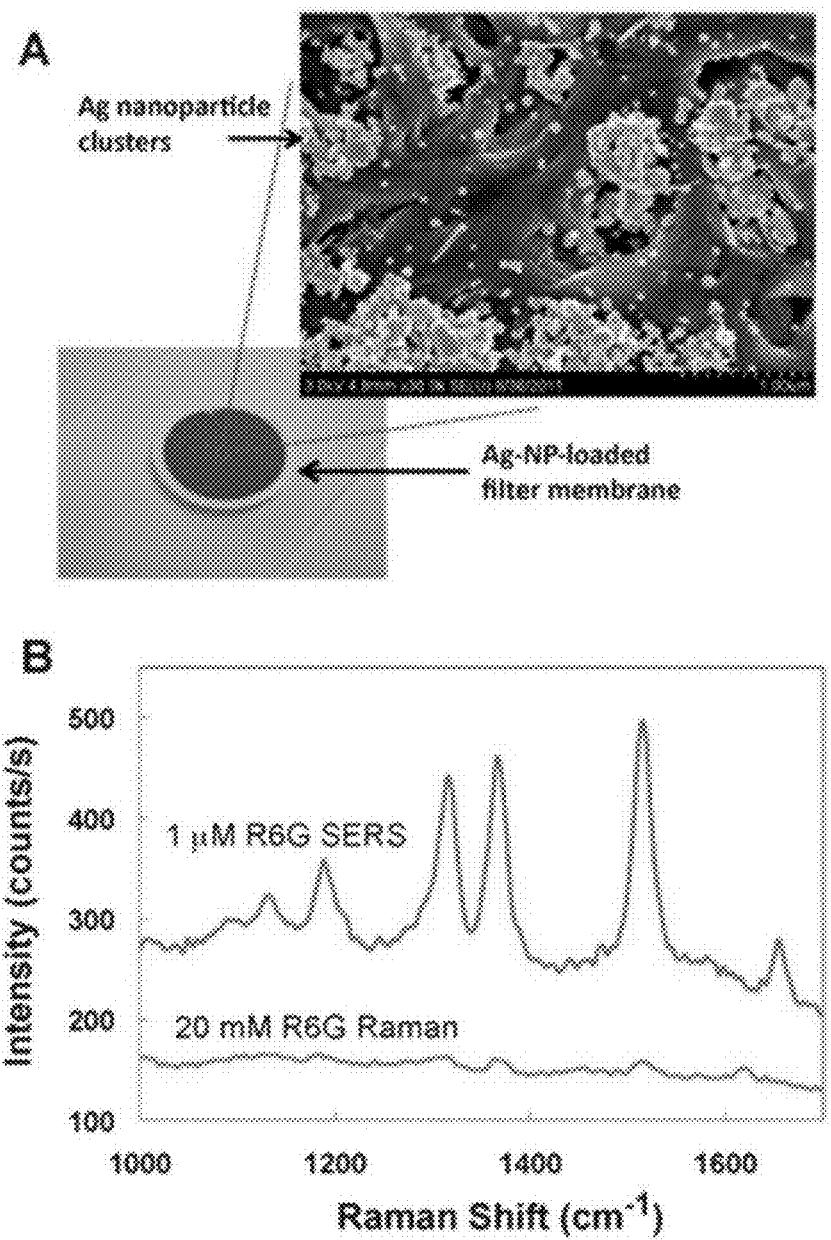
FIG. 6A illustrates an Ag NP-loaded filter membrane (bottom), and an SEM image of a portion thereof showing the clustering of Ag NP in the pores of the filter membrane.
FIG. 6B is a graph illustrating measured Raman spectra with and without loading silver colloid through the membrane (showing Raman signal measurements for 1 µM R6G dried onto the membrane with Ag NPs, and for 20 mM R6G dried onto a membrane with no Ag NPs).

A silver-nanoparticle-coated filter membrane is shown in FIG. 6A. It is clearly visible in the SEM image that the silver nanoparticles are trapped within the pores of the filter, yielding clusters of nanoparticles that are highly SERS active.

SERS measurements were acquired from three randomly selected locations within each membrane and repeated over three membranes, giving a total of nine SERS measurements for each analyte concentration. The laser power used was 3 mW for R6G and 10 mW for melamine and malathion. A 1-second CCD exposure was used, with averaging of the SERS signal over 5 signal acquisitions. To determine the signal intensity, the height of the most prominent peak from the Raman bands was calculated (1509 $cm^{-1}$ for R6G, 508 $cm^{-1}$ for malathion and 690 $cm^{-1}$ for melamine). Background contributions are removed from the signal by subtracting the spectrum measured for water from the spectrum measured for the analyte. To establish the SERS enhancement factor of the silver nanoparticle coated membranes, a 1 μL droplet of 20 mM R6G was spotted onto a plain filter membrane; the resulting signal was compared with the SERS signal from 1 μL of 1 μM R6G pipetted onto a filter membrane after loading silver nanoclusters.

Three analytes were used for analysis: R6G, melamine, and malathion. R6G and malathion were used in water, while 0.1% HCl was added to the melamine/water sample before loading to protonate the melamine. For all three analytes, the filter SERS technique was compared with a conventional SERS method. For the conventional method, 1 μL of silver colloid and 5 μL of sample analyte were spotted onto an aluminum foil surface. The Raman spectrum was acquired after the droplet dried onto the surface. To verify that the filter SERS technique generates quantitative data, all concentration curves were fit using the Hill equation with n=1 (Langmuir isotherm) in Origin.

Results and Discussion

The SEM image in FIG. 6A indicates that a high density of SERS-active hot spots exist across the membrane, which will enable a large enhancement as compared to conventional Raman spectroscopy. To quantify the enhancement of the silver-nanocluster-treated membrane, we measured the Raman signal for 1 μM R6G dried onto the membrane with silver nanoparticles and for 20 mM R6G dried onto a membrane with no silver. The two Raman signals are presented in FIG. 6B. The enhancement factor of the membrane is determined by the following equation:

$$EF = \left(\frac{I_{SERS}}{I_{Raman}}\right)\left(\frac{N_{Raman}}{N_{SERS}}\right)$$

where the intensity I is the height of the 1509 cm$^{-1}$ R6G Raman peak and N represents the total number of R6G molecules deposited onto the substrate.

Using the data in FIG. 6B, an enhancement factor of $3\times10^5$ is determined However, according to SEM images, only approximately 20% of the membrane surface is covered by silver nanoclusters; thus, assuming that the analyte molecules are evenly distributed across the membrane, the enhancement of the silver nanoclusters is approximately $1.5\times10^6$.

Figure 7:
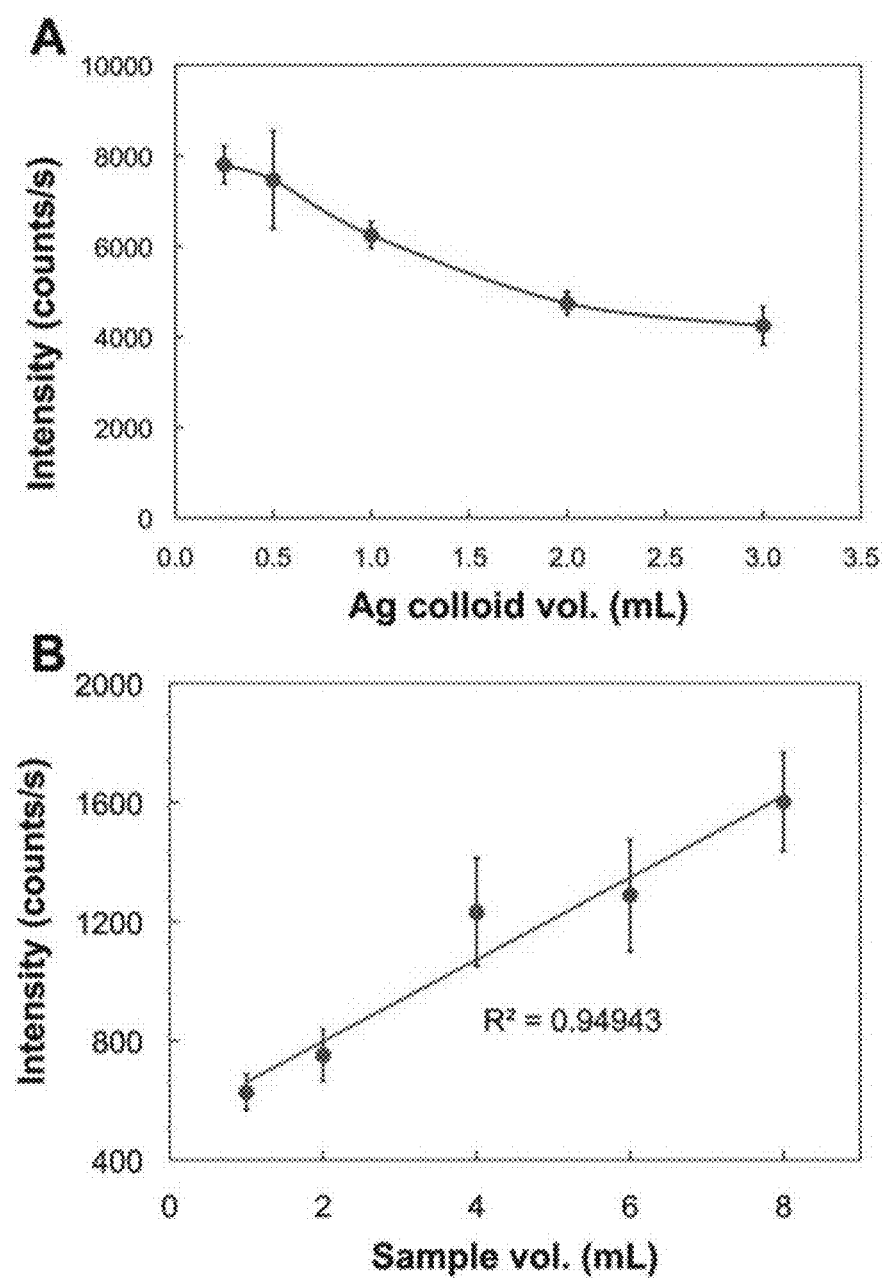
FIGS. 7A and 7B are graphs illustrating measured intensity of the 1509 cm$^{-1}$ R6G Raman peak for increasing volumes of silver colloid loaded into the membrane filter (FIG. 7A), and increasing volumes of sample loaded into the membrane filter (FIG. 7B).

The amount of silver colloid passed through the membrane will affect the SERS activity. The aim is to load enough silver nanoclusters to create a high surface density; however, loading too many silver nanoparticles will cause the membrane to become a relatively thick silver film instead of a plasmonic nanostructured surface. FIG. 7A shows the measured intensity of the 1509 cm$^{-1}$ R6G Raman peak after first loading increasing volumes of silver colloid through the filter and then loading 10 μM R6G.

As shown by the data, the signal intensity decreases significantly when loading more than 0.5 mL of colloid through the filter. However, the variation in signal intensity is higher for 0.5 mL than for larger volumes. Therefore, for all subsequent experiments, we load 1 mL of silver colloid through the membrane before loading the sample through the filter.

Also evaluated was the dependence of the Raman scattering intensity upon sample loading. FIG. 7B shows that the signal increased linearly for increasing sample volume when loading between 1 mL and 8 mL of R6G (1 μM). As expected, this implies that increasing the number of analyte molecules passed through the filter increases the Raman signal. For the experiments in this work, the sample volume was limited to 5 mL, which is a compromise between signal intensity and sample loading time.

Figure 8:
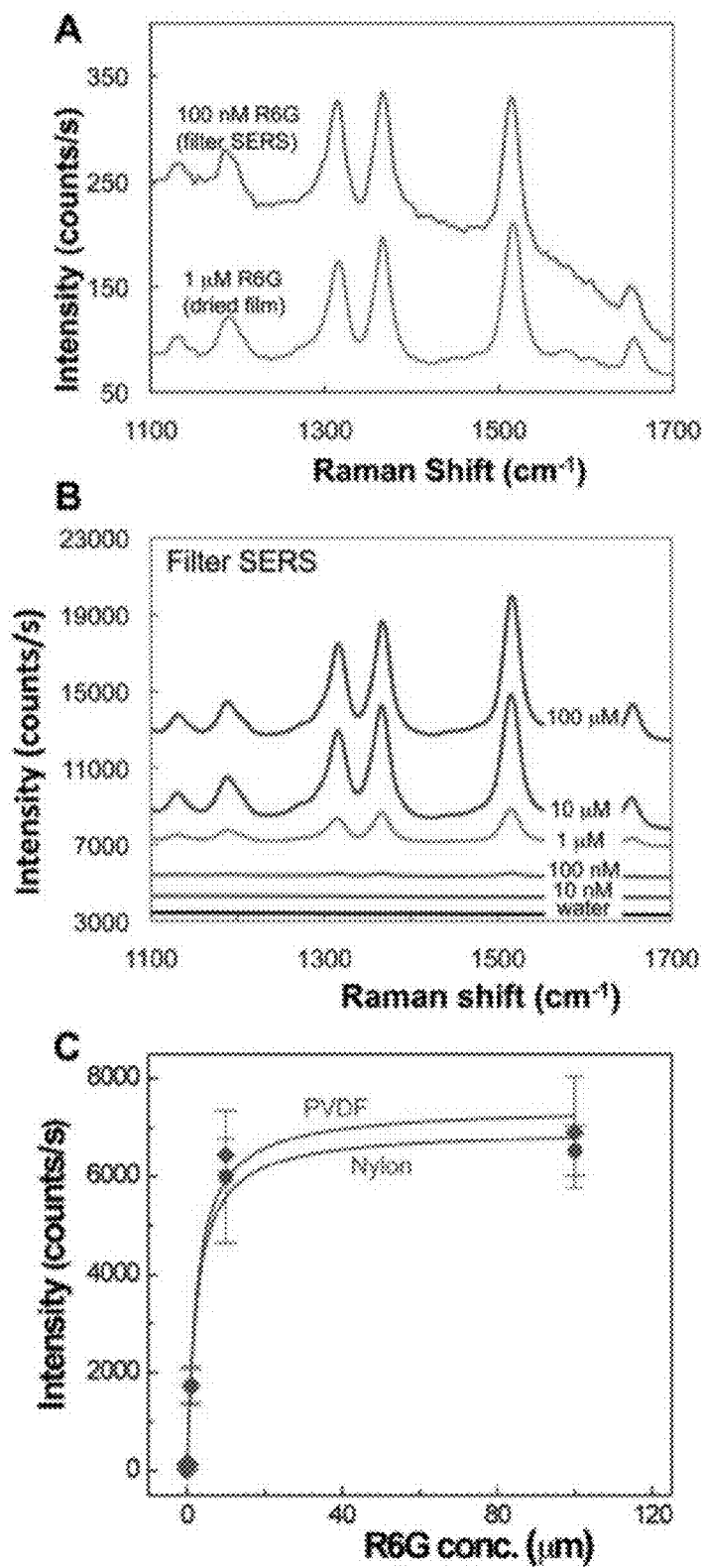
FIGS. 8A, 8B and 8C are graphs illustrating the detection performance of the filter SERS technique for R6G as the analyte.

FIG. 8 presents the detection performance of the filter SERS technique for R6G as the analyte. In FIG. 8A, the detection performance of filter SERS is compared with that of a typical SERS measurement, in which the sample of R6G is added to a silver colloid and dried onto a surface. The measured Raman signals in FIG. 8A show that the signal intensity for 1 μM R6G in colloid dried onto a surface is similar to the signal intensity for 100 nM R6G using the filter SERS technique. Thus, for the case of R6G, the filter SERS technique enables an order of magnitude improvement in detection performance as compared to typical SERS measurements.

To determine the detection limit for R6G using the filter SERS technique, we prepared dilutions of R6G in water from 100 μM down to 10 nM. FIG. 8B shows recorded Raman spectra for this range of R6G concentrations. Data points representing the peak height of the 1509 cm$^{-1}$ R6G Raman peak are plotted against R6G concentration in FIG. 8C. Data for both the nylon and PVDF membranes are plotted and analyzed; minimal difference was observed between the two membranes. In the plot, the data points represent the mean value for three separate membranes, and the value associated with each membrane is the mean across three separate spots on the membrane (i.e., nine data points are taken for each concentration).

Figure 9:
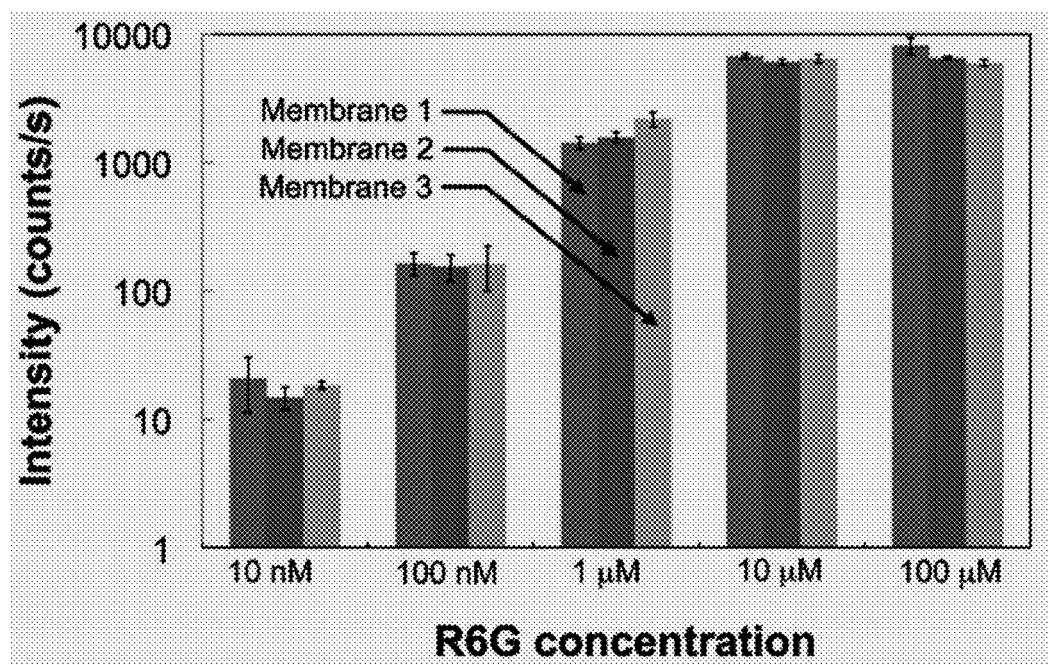
FIG. 9 is a graph illustrating the variation of the SERS intensity of the 1509 cm$^{-1}$ R6G Raman peak. Each bar represents the mean intensity for a particular concentration from one membrane. The error bars show the standard deviation of the intensity measured at three random spots on the respective membrane.

Error bars represent the standard deviation of the mean values for each membrane. FIG. 9 presents the variation of the signal intensity in more detail. Each bar represents the mean for a particular concentration and a particular membrane (each group of bars showing results for membranes 1, 2 and 3), while the error bar for each bar is the standard deviation of the signal intensity of three spots measured within the respective membrane.

Two important characteristics can be seen in the data plotted in FIG. 8C and in FIG. 9. First, the data in FIG. 8C was fitted with the Langmuir isotherm; the fit is excellent (R2=0.989 for the nylon membrane, R2=0.985 for the PVDF membrane). Second, the standard deviation of each data point is relatively low for SERS measurements. These two facts suggest that the filter SERS method is not only simple and practical, but it also has the potential to be a quantitative technique.

Figure 10:
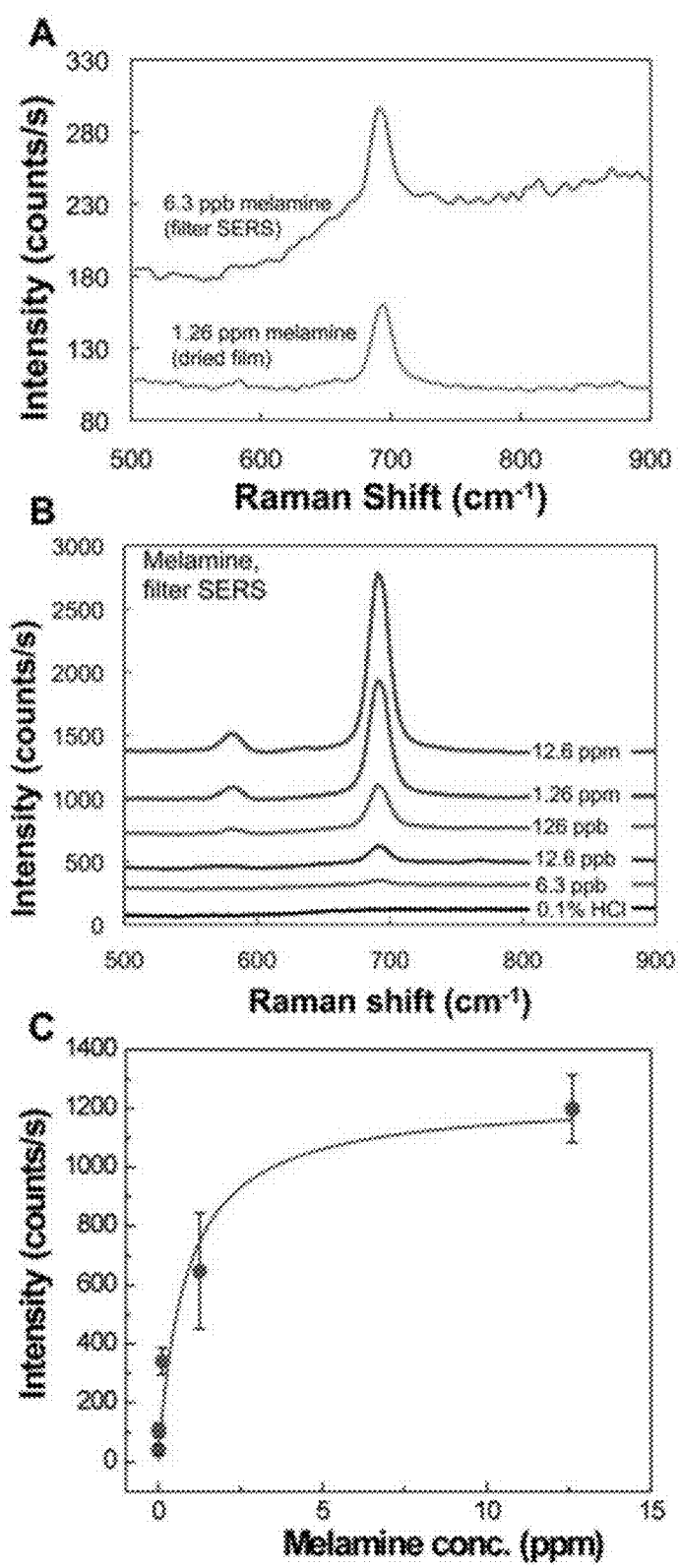
FIGS. 10A, 10B and 10C are graphs illustrating the detection performance for melamine as the analyte.

To demonstrate the use of this practical and portable technique for field-based applications, we performed detection of melamine, a toxic food contaminant, and malathion, a commonly used organophosphate pesticide. The detection performance for melamine is presented in FIG. 10. Referring to FIG. 10A, the signal obtained by filter SERS at 6.3 ppb melamine is compared with the signal measured for 1.26 ppm melamine in silver colloid dried onto a surface. It is evident that the filter SERS technique boosts the detection performance by a factor of 200 as compared to traditional SERS measurements.

FIG. 10B shows the measured SERS spectra for melamine for a concentration range between 12.6 ppm and 6.3 ppb (50 nM) when using the PVDF filter membrane, which proved to be more effective than nylon for melamine detection. The intensity of the 690 cm$^{-1}$ Raman peak for melamine is plotted for each concentration in FIG. 10C. Similar to the case of R6G, the variability of the intensity values is relatively low, and the data can be fit well with a Langmuir isotherm. Even though a portable spectrometer is used for the measurements, the detection limit of 6.3 ppb is achieved, which is well below the currently accepted levels of 2.5 ppm for melamine in foods as established by the FDA, making it possible to use filter SERS as a detection method for melamine in foods.

Figure 11:
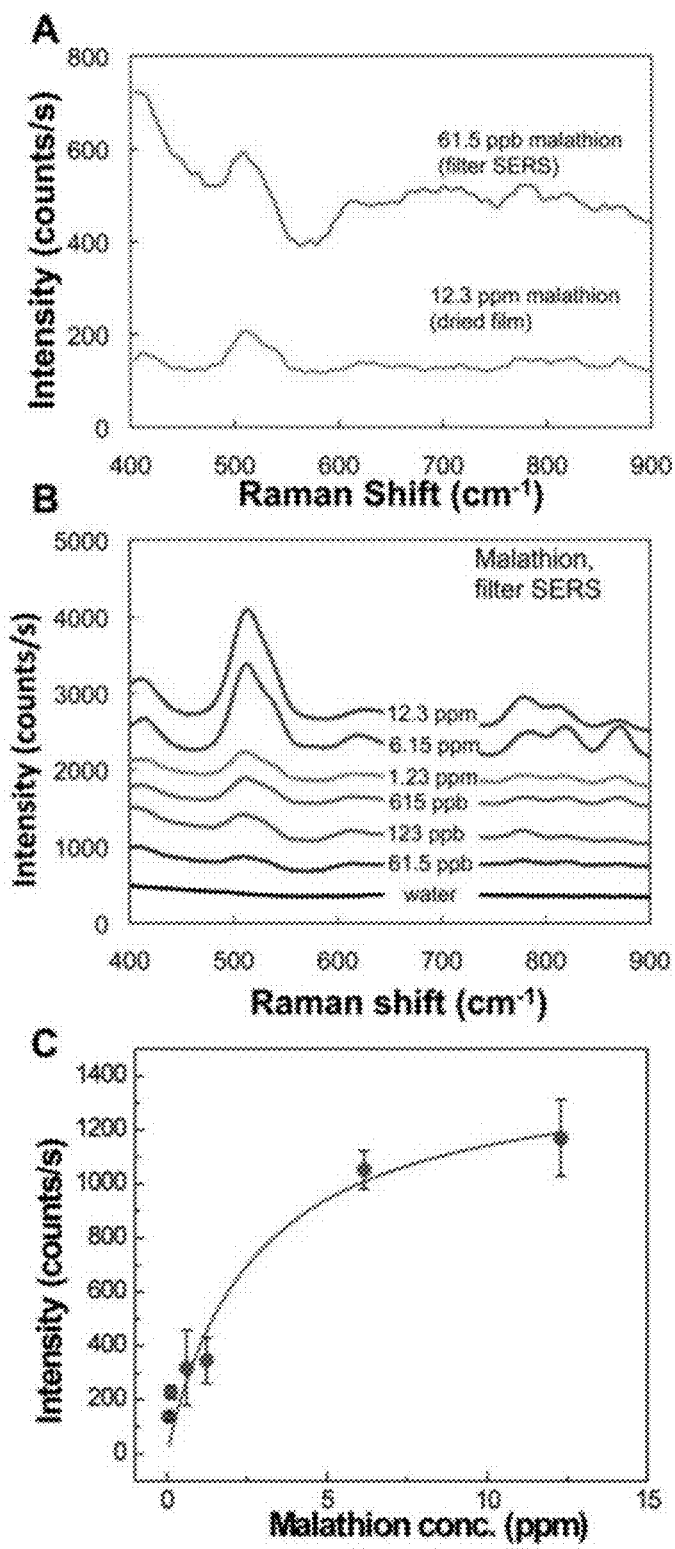
FIG. 11 illustrates graphically the detection performance of filter SERS for the organophosphate malathion in water.

In a similar manner, we analyzed the performance of filter SERS for the detection of the organophosphate malathion in water. As shown in FIG. 11A, by drying a sample of malathion in silver colloid onto a surface, only 12.3 ppm malathion could be detected, while the filter SERS technique enabled the detection of 61.5 ppb, an improvement by a factor of 200. In this case, we used a nylon membrane, which proved to be more effective for malathion detection. The recorded SERS spectra for a malathion concentration range of 12.3 ppm to 61.5 ppb is presented in FIG. 11B. As proven in FIG. 11C, this data can also be fit well by a Langmuir isotherm and exhibits low variability, which suggests that quantitative detection of malathion in water can be performed using our low cost portable SERS detection technique.

We have developed an extremely simple and inexpensive, but highly sensitive method of performing SERS by filtration. The filter membranes create a SERS-active surface by trapping and concentrating nanoparticles from a colloid solution. They also concentrate analytes from relatively large sample volumes into the immobilized matrix of nanoparticles.

The results presented here prove that the filter SERS technique is more sensitive than conventional SERS techniques and that it can be quantitative. Detection limits of 6.3 ppb for melamine and 61.5 ppb for malathion were achieved with this technique. Furthermore, quantitative performance was verified by Langmuir isotherm line fits. This work demonstrates that filter SERS is well suited for low resource settings, in particular, for onsite environmental monitoring and food analysis.

Example 3

Fabrication and Operation of Optofluidic SERS Dipstick

A low-cost commercial piezo-based EPSON inkjet printer was used to print the SERS active substrates on chromatography paper. To form the ink, a silver colloid, prepared by the method of Lee and Meisel (1982), supra, J. Phys. Chem. 86:3391-3395, was concentrated 100× by centrifugation; glycerol and ethanol were added (40% and 10% by volume respectively) to optimize the surface tension and viscosity for optimal printing. The ink was added into re-usable cartridges and printed 10 times onto the desired regions of the paper (FIG. 12a). After printing silver nanoparticles onto the paper, individual dipsticks were cut out of the sheet. The end of the dipstick containing the silver nanoparticles serves as the detection region, while the rest of the paper strip serves as the sample collection zone.

For the dipstick experiments reported here, 5 µL of Rhodamine 6G (R6G) in methanol was added to the sample collection zone. For the surface swab experiments, 5 µL of R6G was spotted randomly over the surface of a clean glass slide. After the sample had dried, the SERS-active paper was soaked with methanol and wiped gently, but firmly over the glass slide (FIG. 12b). In both cases, after the swab-dipstick dried, it was placed into a vial (FIG. 12c) containing 2 mL of methanol; the methanol is quickly wicked up into the swab-dipstick toward the detection tip.

After 15 minutes of run time, the dipstick was dried and SERS measurements were acquired from detection zone. For all SERS measurements, a 785 nm laser (30 mW) was used for excitation, a QE65000 (Ocean Optics) portable spectrometer was used for detection, and a fiber optic probe was used for delivery of laser light and collection of Raman-scattered photons (FIG. 12d).

Results and Discussion

Figure 13:
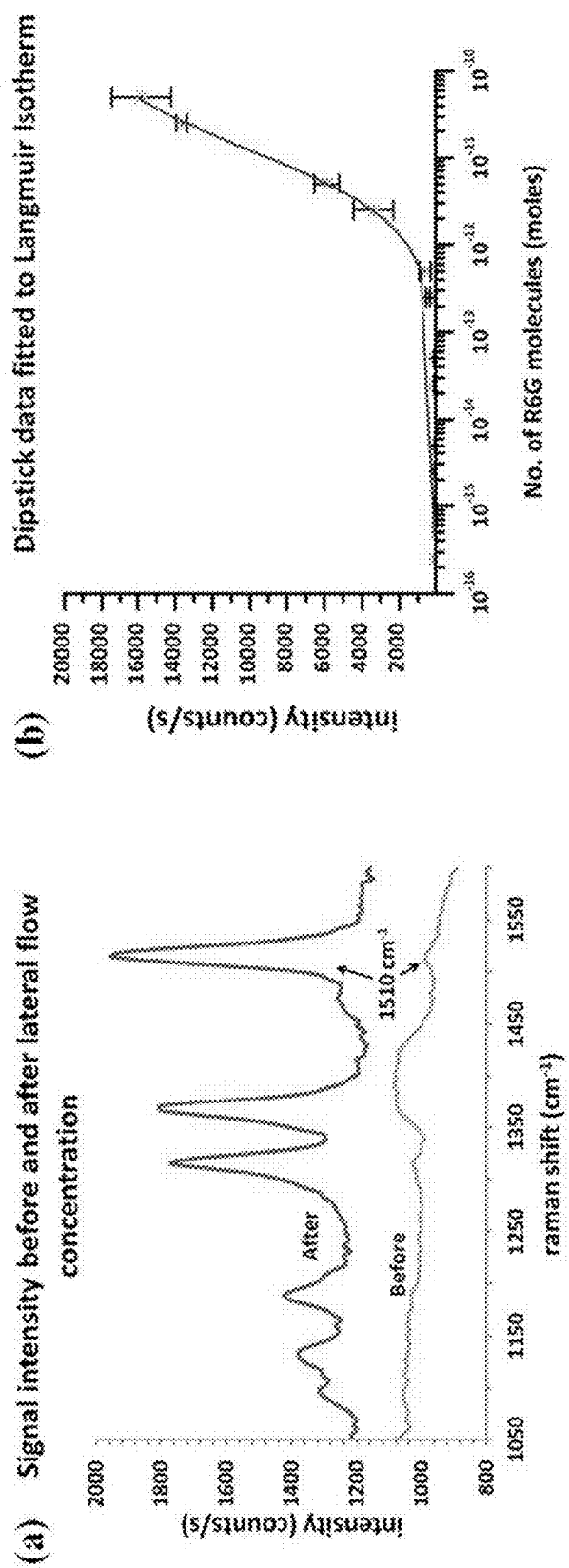
FIG. 13a is a graphical comparison of the SERS signal acquired before and after lateral flow concentration when 250 picomoles of R6G are deposited onto the sample collection region of the paper.
FIG. 13b illustrates graphically the resulting SERS signals after lateral-flow concentration, showing dipstick data at different concentrations of R6G fitted to Langmuir Isotherm by nonlinear curve fitting using Origin. Error bars represent the standard deviation from three different dipsticks.

To demonstrate that the lateral-flow concentration is an integral part of the device, FIG. 13a is a comparison of the SERS signal acquired from applying 250 picomoles of R6G to the Swab-Dipstick before and after performing lateral-flow concentration. Well-known R6G Raman peaks are clearly visible in the post-concentration signal, while it is barely visible in the pre-concentration signal. A comparison of the 1510 cm$^{-1}$ peak shows over 30× improvement to the signal intensity. To show that the swab-dipsticks are quantitative, fixed volumes of varying concentrations of R6G samples are added to the sample collection zone. FIG. 13b shows the resulting SERS signals after lateral-flow concentration. Two important aspects can be gleaned from this figure: (1) the fit of the data to the Langmuir Isotherm is almost perfect (R2=0.99955), indicating that the results are quantitative; and (2) the SERS signal has fairly low variability from substrate to substrate.

Figure 14:
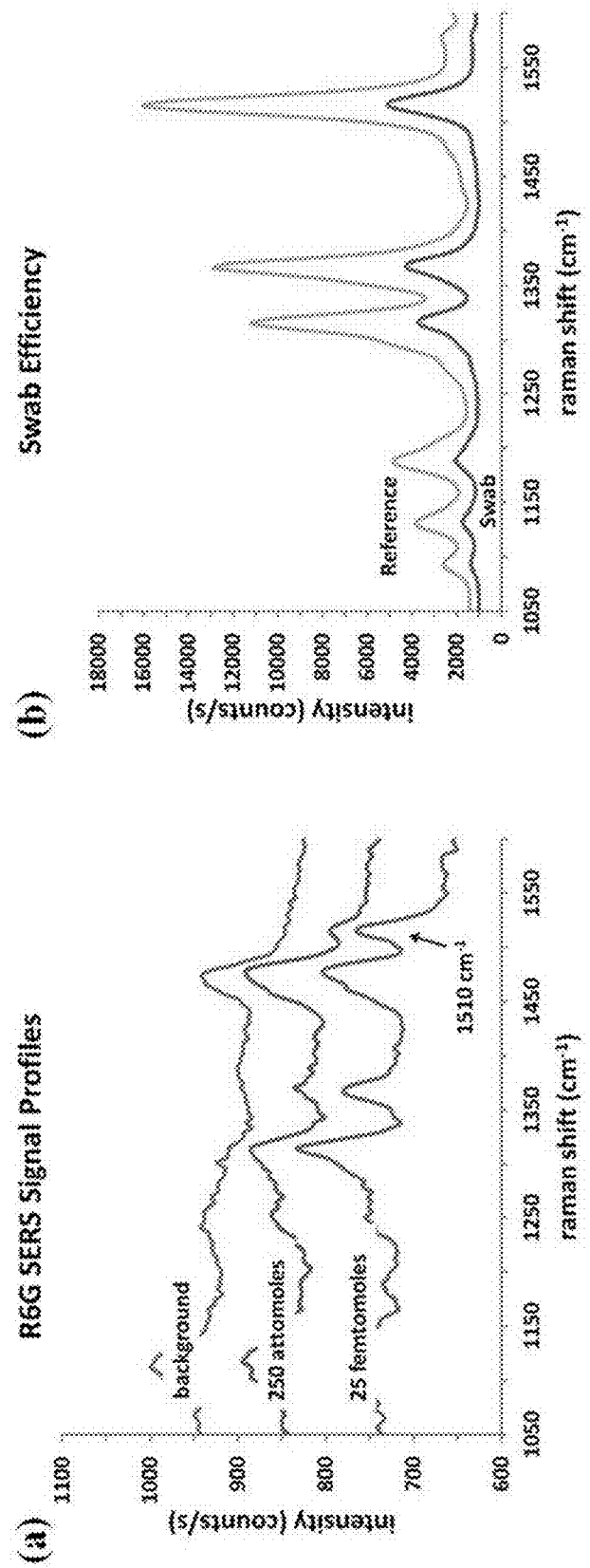
FIG. 14a is a graph illustrating that the SERS signal at 1510 cm$^{-1}$ is clearly detectable even at 250 attomoles of R6G.
FIG. 14b illustrates graphically the resulting SERS signals after lateral-flow concentration, showing SERS signal from swabbing a surface containing R6G compared with the same amount of analyte (250 picomoles) applied directly onto the dipstick.

FIG. 14a shows that the SERS signal from as low as 250 attomoles of R6G was clearly detectable. To compare the efficiency of swabbing, 250 picomoles of R6G was pipetted onto a glass slide and then swabbed; the measured SERS signal was compared with the case when an equal amount of analyte was pipetted directly onto the sample collection zone. After lateral-flow concentration, the signal is easily detectable, although it is reduced as compared to the direct application of analyte (FIG. 14b). This was expected since the swab will not perfectly collect all of the analyte molecules from the surface. The swab efficiency is inherently dependent on the rigorousness of the swabbing. Swabbing is expected to result in signal variability.

We have demonstrated an extraordinarily simple, low-cost analytical technique using a paper swab-dipstick with lateral-flow concentration and SERS detection on an inkjet-printed plasmonic substrate. The paper-based swab dipstick is able to detect at least 250 attomoles of the R6G test analyte. This optofluidic SERS paper device may have immediate applications in on-site sample analysis, including trace chemical detection in liquid samples or on surfaces.

All publications and patents mentioned in this specification are herein incorporated by reference to the same extent as if each individual publication or patent application was specifically and individually indicated to be incorporated by reference in its entirety. While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. A surface enhanced Raman spectroscopy (SERS) analytical device, comprising:
    a substrate having a porous structure, said substrate comprising a material selected from the group consisting of nylon, polyvinylidene fluoride (PVDF), cellulose, modified cellulose, a natural polymer, a synthetic polymer, glass fibers, and a combination thereof; and
    a plurality of plasmonic nanoparticles embedded onto discrete portions of said porous structure, wherein said plasmonic nanoparticles are randomly distributed and form plasmonic nanoparticle clusters, and wherein said plasmonic nanoparticles do not entirely cover a surface of said substrate, and a portion of said surface of said substrate is free from any metal coating.

2. The device of claim 1, wherein said substrate comprises a material selected from the group consisting of cellulose, modified cellulose, a natural polymer, and combinations thereof.

3. The device of claim 1, wherein said plurality of plasmonic nanoparticles form sensing regions spaced from and discretely disposed relative to each other.

4. The device of claim 1, wherein said plasmonic nanoparticles are formed from a material selected from the group consisting of silver, gold, copper, platinum, and combinations thereof.

5. The device of claim 1, wherein said substrate includes at least one of a hydrophilic portion or a hydrophobic portion.

6. The device of claim 1, wherein said plasmonic nanoparticles cover no more than approximately 20% of said surface of said substrate.

7. A method of fabricating a surface enhanced Raman spectroscopy (SERS) device, comprising the steps of:
    providing a substrate having a porous morphology;
    providing a nanoparticle ink solution containing a plurality of plasmonic nanoparticles; and
    depositing the nanoparticle ink solution onto the substrate, thereby embedding the plurality of plasmonic nanoparticles onto the porous substrate to form a SERS analytical device comprising a random distribution of plasmonic nanoparticle clusters, wherein the embedded plasmonic nanoparticles do not entirely cover a surface of the substrate, and a portion of the surface of the substrate is free from any metal coating.

8. The method of claim 7, comprising the further step of modifying at least a portion of the substrate to form at least one of a hydrophobic region or a hydrophilic region.

9. The method of claim 8, wherein said modifying step includes coating at least a portion of the substrate with a substance to form the hydrophobic region or the hydrophilic region.

10. The method of claim 9, wherein said coating includes a process selected from the group consisting of screen printing, inkjet printing, spraying, pipetting, and soaking.

11. The method of claim 7, wherein said nanoparticle ink solution comprises a modifier for controlling at least one of a viscosity and a surface tension of the nanoparticle ink solution.

12. The method of claim 7, wherein said nanoparticle ink solution comprises a modifier for controlling at least one of an aggregation, oxidation, and stability of the plasmonic nanoparticles in the nanoparticle ink solution.

13. The method of claim 7, wherein said depositing step includes a process selected from the group consisting of inkjet printing, screen printing, spraying, and filtering.

14. The method of claim 13, wherein said depositing step includes forming an array of SERS sensing regions at a selected position on the substrate.

15. The method of claim 14, wherein the array comprises a selected pattern of SERS sensing regions spaced from and discretely disposed relative to each other.

16. The method of claim 7, wherein said depositing step includes forming a single SERS sensing region at a selected position on the substrate.

17. A method of detecting a target analyte in a sample, comprising the steps of:
providing a porous membrane having a surface enhanced Raman spectroscopy (SERS) sensing matrix comprising a plurality of plasmonic nanoparticles embedded onto discrete portions of said porous membrane, wherein said plasmonic nanoparticles are randomly distributed and form plasmonic nanoparticle clusters, and wherein said plasmonic nanoparticles do not entirely cover a surface of said porous membrane, and a portion of said surface of said porous membrane is free from any metal coating, and wherein said porous membrane comprises a material selected from the group consisting of nylon, polyvinylidene fluoride (PVDF), cellulose, modified cellulose, a natural polymer, a synthetic polymer, glass fibers, and a combination thereof;
contacting the sample with said porous membrane, whereby the target analyte, if present in the sample, is concentrated in said SERS sensing matrix; and
analyzing said porous membrane after said contacting step using SERS detection equipment.

18. The method of claim 17, wherein said plasmonic nanoparticles are formed from a material selected from the group consisting of silver, gold, copper, platinum, and combinations thereof.

19. The method of claim 17, wherein said contacting step includes a process selected from the group consisting of pipetting the sample onto said porous membrane, passing the sample through said porous membrane, swabbing the porous membrane over a surface containing the sample, and dipping the porous membrane into the sample.

20. The method of claim 17, comprising the further step of dipping the porous membrane into a solvent, thereby concentrating via lateral flow the target analyte, if present in the sample.

21. The method of claim 17, wherein said SERS detection equipment comprises a spectrometer, an excitation source, and an optical device.

22. The method of claim 17, wherein said porous membrane comprises a material selected from the group consisting of cellulose, modified cellulose, a natural polymer, and a combination thereof.

23. A kit for detecting a target analyte, comprising:
a solution comprising plasmonic nanoparticles;
a porous membrane configured to trap and concentrate said plasmonic nanoparticles onto discrete portions of said porous membrane and form a random distribution of plasmonic nanoparticle clusters that do not entirely cover a surface thereof when said solution passes through said porous membrane, wherein a portion of said surface thereof is free from any metal coating, thereby forming surface enhanced Raman spectroscopy (SERS) sensing regions spaced from and discretely disposed relative to each other;
a pump configured to hold a sample being tested for target analyte; and
a filter holder configured to retain said porous membrane, wherein the sample in said pump is passable through said porous membrane when said porous membrane is retained by said filter holder, so that the target analyte, if present in the sample, is concentrated in said SERS sensing region.

24. The kit of claim 23, wherein said porous membrane comprises a material selected from the group consisting of nylon, polyvinylidene fluoride (PVDF), cellulose, modified cellulose, a natural polymer, a synthetic polymer, glass fibers, and combinations thereof.

25. The kit of claim 23, wherein said plasmonic nanoparticles are formed from a material selected from the group consisting of silver, gold, copper, platinum, and combinations thereof.

26. The kit of claim 23, wherein said pump is additionally configured to hold said solution, said solution passable through said porous membrane to form said SERS sensing region when said porous membrane is retained by said filter holder.

* * * * *